(12) United States Patent
Miller et al.

(10) Patent No.: US 7,652,142 B2
(45) Date of Patent: Jan. 26, 2010

(54) BIPIPERIDINYL DERIVATIVES USEFUL AS INHIBITORS OF CHEMOKINE RECEPTORS

(75) Inventors: Michael W. Miller, Scotch Plains, NJ (US); Jack D. Scott, Scotch Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 402 days.

(21) Appl. No.: 10/979,075

(22) Filed: Nov. 1, 2004

(65) Prior Publication Data

US 2006/0025441 A1 Feb. 2, 2006

Related U.S. Application Data

(60) Provisional application No. 60/516,954, filed on Nov. 3, 2003.

(51) Int. Cl.
*A61K 31/4545* (2006.01)
*C07D 401/04* (2006.01)

(52) U.S. Cl. .................. 546/187; 546/191; 544/335; 514/256; 514/316

(58) Field of Classification Search .................. 546/208, 546/187, 191; 514/316, 256; 544/335
See application file for complete search history.

(56) References Cited

U.S. PATENT DOCUMENTS

| | | | |
|---|---|---|---|
| 5,883,096 A | 3/1999 | Lowe et al. | |
| 5,889,006 A | 3/1999 | Lowe et al. | |
| 5,952,349 A | 9/1999 | Asberom et al. | |
| 5,977,138 A | 11/1999 | Wang et al. | |
| 6,037,352 A | 3/2000 | Lowe et al. | |
| 6,387,930 B1 | 5/2002 | Baroudy et al. | |
| 6,391,865 B1 | 5/2002 | Baroudy et al. | |
| 6,602,885 B2 | 8/2003 | Baroudy et al. | |
| 7,384,948 B2 * | 6/2008 | Palani et al. | 514/256 |
| 7,442,703 B2 * | 10/2008 | Palani et al. | 514/256 |
| 2004/0010008 A1 | 1/2004 | Palani et al. | |
| 2004/0092551 A1 | 5/2004 | Palani et al. | |
| 2004/0092745 A1 | 5/2004 | Palani et al. | |

FOREIGN PATENT DOCUMENTS

| | | |
|---|---|---|
| WO | WO 00/66558 | 11/2000 |
| WO | WO00/66558 | 11/2000 |
| WO | WO02/079194 | 10/2002 |
| WO | WO02/081449 | 10/2002 |
| WO | WO 02/081449 A1 | 10/2002 |
| WO | WO 03/020716 | * 3/2003 |
| WO | WO03/020716 | 3/2003 |
| WO | WO03/069252 | 8/2003 |
| WO | WO 03/069252 A1 | 8/2003 |

OTHER PUBLICATIONS

Dorwald F. A. Side Reactions in Organic Synthesis, 2005, Wiley: VCH, Weinheim p. IX of Preface., p. 41.*
Hutchins, R.O. et. al. Journal of Organic Chemistry 1977, 42, 82-91.*
Thoma, et. al. "Orally Bioavailable Competitive CCR5 Antagonists" Journal of Medicinal Chemistry 2004, 47, 1939-1955.*
Martin, Yvonne C. et. al. "Do Structurally Similar Molecules Have Similar Biological Activity?" Journal of Medicinal Chemistry 2002, 45, 4350-4358.*
Vandamme, A-M, et al., "Anti-human Immunodeficiency virus drug combination strategies," Antiviral Chemistry & Chemotherapy 9:187-203 (1998).
International Search Report for PCT/US2004/036273 dated Jun. 15, 2005.
Debnath, Asim Kumar, Generation of Predictive Pharmacophore Models for CCR5 Antagonists: study with Piperidine- and Piperazine-Based Compounds as a New Class of HIV-1 Entry Inhibitors, J. Med. Chem. 2003, 4501-4515, 46(21).
Vandamme, A-M, et. al., Anti-human imrnunodeficiency virus drug combination strategies, Antiviral Chemistry & Chemotherapy, 1998, 187-203, 9.

* cited by examiner

*Primary Examiner*—Rita J Desai
*Assistant Examiner*—David K O'Dell
(74) *Attorney, Agent, or Firm*—Krishna G. Banerjee; Palaiyur S. Kalyanaraman

(57) ABSTRACT

In its many embodiments, the present invention provides a novel class of bipiperidinyl compounds as inhibitors of the CCR5 receptors, methods of preparing such compounds, pharmaceutical compositions containing one or more such compounds, methods of preparing pharmaceutical formulations comprising one or more such compounds, and methods of treatment, prevention, inhibition, or amelioration of one or more diseases associated with CCR5 using such compounds or pharmaceutical compositions. The invention also relates to the use of a combination of a compound of this invention and one or more antiviral or other agents useful in the treatment of Human Immunodeficiency Virus (HIV). The invention further relates to the use of a compound of this invention, alone or in combination with another agent, in the treatment of solid organ transplant rejection, graft v. host disease, arthritis, rheumatoid arthritis, inflammatory bowel disease, atopic dermatitis, psoriasis, asthma, allergies or multiple sclerosis.

14 Claims, No Drawings

BIPIPERIDINYL DERIVATIVES USEFUL AS INHIBITORS OF CHEMOKINE RECEPTORS

FIELD OF THE INVENTION

The present invention relates to bipiperidinyl compounds useful as selective inhibitors of chemokine receptors, especially of the CCR5 receptors, pharmaceutical compositions containing the compound of this invention, and methods of treatment using the inventive compounds. The invention also relates to the use of a combination of the compound of this invention and one or more antiviral or other agents useful in the treatment of Human Immunodeficiency Virus (HIV). The invention further relates to the use of the compound of this invention, alone or in combination with another agent, in the treatment of solid organ transplant rejection, graft v. host disease, arthritis, rheumatoid arthritis, inflammatory bowel disease, atopic dermatitis, psoriasis, asthma, allergies or multiple sclerosis. This application claims priority from U.S. provisional patent application, Ser. No. 60/516,954 filed on Nov. 3, 2003.

BACKGROUND OF INVENTION

The global health crisis caused by HIV, the causative agent of Acquired Immunodeficiency Syndrome (AIDS), is unquestioned. While recent advances in drug therapies have been successful in slowing the progression of AIDS, there is still a need to find a safer, more efficient, less expensive way to control the virus.

It has been reported that the CCR5 (CC Chemokine Receptor 5) gene plays a role in resistance to HIV infection. HIV infection begins by attachment of the virus to a target cell membrane through interaction with the cellular receptor CD4 and a secondary chemokine co-receptor molecule, and proceeds by replication and dissemination of infected cells through the blood and other tissue. There are various chemokine receptors, but for macrophage-tropic HIV, believed to be the key pathogenic strain that replicates in vivo in the early stages of infection, the principal chemokine receptor required for the entry of HIV into the cell is CCR5. Therefore, interfering with the interaction between the viral receptor CCR5 and HIV can block HIV entry into the cell. The present invention relates to small molecules which are CCR5 antagonists.

CCR5 receptors have been reported to mediate cell transfer in inflammatory diseases such as arthritis, rheumatoid arthritis, atopic dermatitis, psoriasis, asthma and allergies. Inhibitors of such receptors are expected to be useful in the treatment of such diseases, and in the treatment of other inflammatory diseases or conditions such as inflammatory bowel disease, multiple sclerosis, solid organ transplant rejection and graft v. host disease.

Other piperidine derivatives, which are muscarinic antagonists useful in the treatment of cognitive disorders such as Alzheimer's disease, are disclosed in U.S. Pat. Nos. 5,883, 096, 6,037,352, 5,889,006, 5,952,349, and 5,977,138.

Compounds useful as CCR5 receptor antagonists are disclosed in U.S. Pat. Nos. 6,387,930; 6,602,885 and 6,391,865, PCT Publications WO2000/66558 and WO2003/69252, and in pending patent applications, Ser. No. 10/229,466, filed Aug. 28, 2002; Ser. No. 10/629,466 filed Jul. 29, 2003, and Ser. No. 10/628,933 filed Jul. 29, 2003.

PCT Publication WO2002/081449 published Oct. 17, 2002 (R. Albert et al), discloses certain bipiperidinyl derivatives useful as chemokine receptor inhibitors.

A-M. Vandamme et al., *Antiviral Chemistry & Chemotherapy*, 9:187-203 (1998) disclose current clinical treatments of HIV-1 infections in man including at least triple drug combinations, or so-called Highly Active Antiretroviral Therapy ("HAART"). HAART involves various combinations of nucleoside reverse transcriptase inhibitors ("NRTI"), non-nucleoside reverse transcriptase inhibitors ("NNRTI") and HIV protease inhibitors ("PI"). In compliant drug-naive patients, HAART is effective in reducing mortality and the progression of HIV-1 to AIDS. However, these multidrug therapies do not eliminate HIV-1 and long-term treatment usually results in multidrug resistance. Development of new drug therapies to provide better HIV-1 treatment remains a priority.

SUMMARY OF THE INVENTION

The present invention provides a novel class of compounds as antagonists of the CCR5 receptor, methods of preparing such compounds, pharmaceutical compositions containing one or more such compounds, and methods of treatment, prevention or amelioration of one or more diseases associated with the CCR5 receptor.

One aspect of the invention relates to a compound having the general structure shown in Formula I:

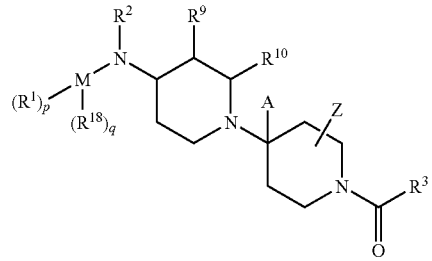

Formula I or a pharmaceutically acceptable salt, solvate or ester thereof; wherein:

p is a number from 1-4;
q is a number from 0-4;
M is aryl substituted with $R^1$ and optionally substituted with $R^{18}$, or heteroaryl substituted with $R^1$ and optionally substituted with $R^{18}$, or N(alkyl)pyridone with the proviso that when M is N(alkyl)pyridone, then p is 0-4 with said p moieties being the same or different, each p moiety being independently selected from the $R^1$ and $R^{18}$ moieties;
$R^1$ is selected from the group consisting of:
 -alkyl-C(O)-heterocyclyl,
 -alkyl-CN,
 -alkyl-N(C=O)-alkyl-N($R^4R^5$),
 -alkyl-N(C=O)-alkyl(aryl)-N($R^4R^5$),
 -alkyl-N(C=O)-heterocyclyl,
 -alkyl-N(C=O)-heteroalkyl,
 -alkyl-N(C=O)-alkyl(hydroxy)(aryl),
 -alkyl-N(C=O)—C(=O)(aryl),
 -alkyl-N(C=O)—C(=O)(alkyl),
 -alkyl-N(C=O)—C(=O)(heteroaryl),
 -heterocyclyl,
 -alkoxy-C(O)X,
 -alkyl-$SO_2$-alkyl-N($R^4R^5$);
 -haloalkyl-C(O)$OR^5$,
 -haloalkyl-C(O)—N($R^5R^6$),
 -alkyl-S($O_2$)$R^5$, —S(O₂)(hydroxyalkyl),
-alkyl-C(O)R⁵,
-alkyl-C(R⁵)(=N—OR⁶),
—N(C=O)-alkyl-N(CHR⁴R⁵), and
—S(O₂)(heterocyclyl);

R² is selected from the group consisting of H, alkyl, aryl, arylalkyl, heteroarylalkyl, alkylketone, arylketone, alkyl, haloalkyl, cycloalkyl, heterocyclyl, cycloalkylalkyl, alkylsulfonyl, arylsulfonyl, alkoxyalkyl, or amide;

R³ is selected from the group consisting of aryl, 6-membered heteroaryl, fluorenyl; and diphenylmethyl, 6 membered heteroaryl-N-oxide,

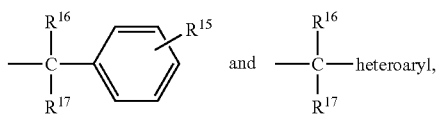

wherein each of said aryl, fluorenyl, diphenyl and heteroaryl is unsubstituted or optionally independently substituted with 1-4 substituents which can be the same or different each substituent being independently selected from the group consisting of R¹¹, R¹², R¹³, R¹⁴ and R¹⁵;

R⁴ is selected from the following group consisting of H, alkyl, cycloalkyl, heterocyclyl, hydroxyalkyl, aryl, heteroaryl, alkyloxy, S(O₂)alkyl, S(O₂)cycloalkyl, S(O₂)arylalkyl, S(O₂)aryl, C(O)alkyl, C(O)aryl, C(O)arylalkyl, C(O)cycloalkyl and C(O)NR⁵R⁶;

R⁵ and R⁶ can be the same or different, each being independently selected from the following group consisting of H, alkyl, cycloalkyl, heterocyclyl, aryl, arylalkyl and heteroaryl;

X is heterocyclyl, NR⁵R⁶, —O(alkyl), —O(Cycloalkyl) or —OH;

R⁹, R¹⁰ and Z can be the same or different each being independently selected from the group consisting of hydrogen, alkyl, and -haloalkyl;

R¹¹ and R¹² can be the same or different each being independently selected from the group consisting of alkyl, -haloalkyl, halogen, —NR¹⁹R²⁰, —OH, —CF₃, —OCH₃, —O-acyl, and —OCF₃;

R¹³ is selected from the group consisting of hydrogen, H, R¹¹, phenyl, —NO₂, —CN, —CH₂F, —CHF₂, —CHO, —CH=N(OR¹⁹), pyridyl-N-oxide, pyrimidinyl, pyrazinyl, —N(R²⁰)C(O)N(R²⁰R²¹), —N(H)C(O)N(H)(chloroalkyl), —N(H)C(O)N(H)(cycloalkylalkyl), —N(H)C(O)alkyl, —N(H)C(O)CF₃, —N(H)S(O₂)N(alkyl)₂, —N(H)S(O₂)alkyl, —N(H)S(O₂)cycloalkyl, —N(SO₂CF₃)₂, —N(H)C(O)Oalkyl, -cycloalkyl, —SR²² —S(O)R²², —S(O₂)R²², —S(O₂)N(H)(alkyl), —O—S(O₂)alkyl, —O—S(O₂)CF₃, hydroxyalkyl, —C(O)N(R¹⁹R²⁰), —C(O)N(CH₂CH₂—O—CH₃)₂, —OC(O)N(H)(alkyl), —C(O)OR¹⁹, —Si(CH₃)₃ and —B(OC(CH₃)₂)₂;

R¹⁴ is selected from the group consisting of alkyl, -haloalkyl-NH₂ and R¹⁵-substituted phenyl;

R¹⁵ is 1-3 substituents which can be the same or different each being independently selected from the group consisting of hydrogen, -alkyl, -haloalkyl, —CF₃, —C(O)OR²⁰, —CN, alkoxy and halogen;

R¹⁶ and R¹⁷ can each be the same or different each being independently selected from the group consisting of hydrogen and alkyl, or R¹⁶ and R¹⁷ together are a C₂-C₅ alkylene group and with the carbon to which they are attached form a spiro ring of 3 to 6 carbon atoms;

R¹⁹, R²⁰ and R²¹ can each be the same or different and are each independently selected from the group consisting of H, alkyl, aryl, arylalkyl, and cycloalkyl;

R²² is selected from the group consisting of alkyl, -haloalkyl, (C1-C6)hydroxyalkyl, alkylene, cycloalkyl, aryl and arylalkyl-;

R¹⁸ is selected from the group consisting of halo, alkyl, haloalkyl, alkoxy, cycloalkyl, heterocyclyl, amido, —CF₃, OCF₃, aryl, heteroaryl, —YR²³, —C(=O)(C₃-C₈cycloalkyl), —C(=O)(C₃-C₈heterocyclyl), —(C₁-C₆)alkyl-N(R²⁴)SO₂R²⁵, —(C₁-C₆)alkyl-C(O)NR²⁶R²⁴, —CN, —CO₂H, —CO₂R²⁵, (R²⁷)aryl(C₁-C₆)alkyl-, (R²⁷)heteroaryl(C₁-C₆)alkyl-, —C(=O)—(C₁-C₆)alkyl, (R²⁷)aryl-C(=O)—, —C(=O)NR²⁴R²⁵, —C(=O)NH₂, —C(=O)N(H)OH, —(C₁-C₆)alkyl-N(R²⁴)C(=O)R²⁵, —(C₁-C₆)alkyl-N(R²⁴)CO₂R²⁵, —(C₁-C₆)alkyl-N(R²⁴)C(=O)NR²⁴R²⁵, —(C₁-C₆)alkyl-NR²⁴R²⁵, —(C₁-C₆)alkyl-NH₂, —(C₁-C₆)alkylSO₂NR²⁴R²⁵ and —SO₂NR²⁴R²⁵, wherein R¹⁸ can be the same or different and is independently selected when there is more than one R¹⁸ present;

R²³ is selected from the group consisting of aryl, substituted aryl, heteroaryl, alkyl, haloalkyl and cycloalkyl;

R²⁶ and R²⁴ can each be the same or different and are each independently selected from the group consisting of H, (C₁-C₆)alkyl and (C₃-C₆)cycloalkyl;

R²⁵ is selected from the group consisting of (C₁-C₆)alkyl, —(C₁-C₆)haloalkyl, —(C₂-C₆)hydroxyalkyl, —(C₂-C₆)alkylene, —(C₃-C₆)cycloalkyl, -aryl and -aryl(C₁-C₆)alkyl;

R²⁷ is 1, 2 or 3 substituents selected from the group consisting of H, halo, (C₁-C₆)alkyl, (C₁-C₆)alkoxy, —CF₃, —OCF₃, CH₃C(O)—, —CN, CH₃SO₂—, CF₃SO₂— and —NH₂, wherein R²⁷ can be the same or different and is independently selected when there are more than one R²⁷ present;

Y is S(O₂), S, S(O), O or CH₂;

and

A is selected from the group consisting of H, alkyl, and alkenyl.

The term "spiro ring" refers to moieties such as, for example, the following illustration:

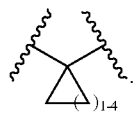

The depicted moieties —(R²⁷)aryl, and —(R²⁷)heteroaryl mean that (R²⁷) represents the substituent(s) on the aryl and heteroaryl respectively.

The compounds of Formula I can be useful as CCR5 inhibitors and in the treatment and prevention of diseases associated with CCR5 and Human Immunodeficiency Virus.

DETAILED DESCRIPTION OF THE INVENTION

In one embodiment, the present invention discloses bipiperidinyl compounds which are represented by structural Formula I, or a pharmaceutically acceptable salt, solvate or ester thereof, wherein the various moieties are as described above.

In an embodiment, M is a substituted aryl.

In another embodiment, M is a substituted heteroaryl.

In another embodiment, R¹ is selected from the group consisting of:

—(C1-C6)alkyl-C(O)-heterocyclyl,
—(C1-C6)alkyl-CN,
—(C1-C6)alkyl-N(C=O)—(C1-C6)alkyl -N(R$^4$R$^5$),
—(C1-C6)alkyl-N(C=O)—(C1-C6)alkyl (aryl)-N(R$^4$R$^5$),
—(C1-C6)alkyl—N(C=O)-heterocyclyl,
—(C1-C6)alkyl-N(C=O)heteroalkyl,
—(C1-C6)alkyl-N(C=O)-heteroalkyl,
—(C1-C6)alkyl-N (C=O)—(C1C6)alkyl(hydroxy)(aryl),
—(C1-C6)alkyl-N(C=O)—C(=O)(aryl),
—(C1-C6)alkoxy-C(O)X,
—(C1-C6)alkyl-SO$_2$—(C1-C6)alkyl-N(R$^4$R$^5$);
-halo(C1-C6)alkyl-C(O)OR$^5$,
-halo(C1-C6)alkyl-C(O)—N(R$^5$R$^6$),
—(C1-C6)alkyl-S(O$_2$)R$^5$,
—S(O$_2$)(hydroxy(C1-C6)alkyl),
—(C1-C6)alkyl-C(O)R$^5$,
—(C1-C6)alkyl-C(R$^5$)(=N—OR$^6$),
—N(C=O)—(C1-C6)alkyl —N(CR$^4$R$^5$), and
—S(O$_2$)(heterocyclyl).

In another embodiment, M is an aryl.
In another embodiment, M is a phenyl substituted with one R$^1$ moiety.
In another embodiment, p is a number from 1 to 3.
In another embodiment, p is 1.
In another embodiment, M is a didehydropiperidone substituted with one R$^1$ moiety.
In another embodiment, q is 0.
In another embodiment, R$^1$ is selected from the group consisting of:
—CH$_2$—N(C=O)-morpholine,
—CH(CH$_3$)—N(C=O)-morpholine,
—C(CH$_3$)$_2$—C(=O)-pyrrolidine,
—C(CH$_3$)$_2$—C(=O)-piperidine,
-pyrrolidinone,
-piperidinone, and
-oxazolidinone.

In another embodiment, R$^2$ is a phenyl.
In another embodiment, R$^2$ is phenethyl.
In another embodiment, R$^3$ is a substituted phenyl or substituted pyrimidine.
In another embodiment, R$^3$ is a phenyl substituted with one or more moieties which can be same or different each being independently selected from the group consisting of alkyl, urea, amine and sulfonamide.
In another embodiment, R$^4$ is an alkyl, hydroxyalkyl, SO$_2$alkyl or C(O)NR$^5$R$^6$.
In another embodiment, A is methyl.
In another embodiment, Z is H.
In another embodiment, M is phenyl; R$^1$ is —(CH$_2$)—C(O)-heterocyclyl, —(CH$_2$)CN, —(CH$_2$)—N(C=O)-heterocyclyl, —(CH$_2$)—N(C=O)—CH$_2$-heterocyclyl, —(CH$_2$)—SO$_2$—CH$_2$—NR$^4$R$^5$, or —(CH$_2$)—C(R$^5$)(=N—OR$^6$); R$^3$ is a substituted pyrimidine, X is a heterocyclyl, and A is methyl.
In another embodiment, q is 0.
In another embodiment, Y is S(O$_2$).

As used above, and throughout this disclosure, the following terms, unless otherwise indicated, shall be understood to have the following meanings:

"Patient" includes both human and animals.
"Mammal" means humans and other mammalian animals.
"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The alkynyl group may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

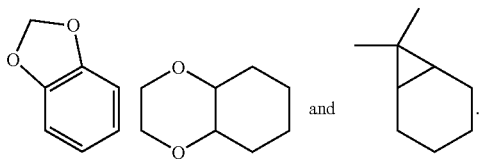

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

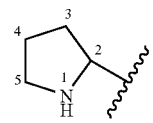

there is no —OH attached directly to carbons marked 2 and 5.

It should also be noted that tautomeric forms such as, for example, the moieties:

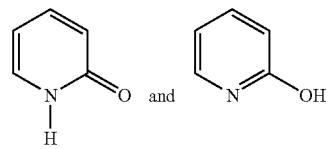

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl—S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the diseases noted above and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Compounds of Formula I, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester, and prodrug of enantiomers, stereoisomers, rotamers, tautomers, positional isomers, racemates or prodrugs of the inventive compounds.

Polymorphic forms of the compounds of Formula I, and of the salts, solvates, esters and prodrugs of the compounds of Formula I, are intended to be included in the present invention.

The compounds of Formula I can be useful as CCR5 inhibitors and in the treatment and prevention of diseases associated with CCR5 and Human Immunodeficiency Virus. They can be useful for the treatment, prevention and/or amelioration of diseases such as, for example, Acquired Immune Deficiency Syndrome ("AIDS"), solid organ transplant rejection, graft v. host disease, arthritis, rheumatoid arthritis, inflammatory bowel disease, atopic dermatitis, psoriasis, asthma, allergies or multiple sclerosis. Thus, an aspect of the invention relates to a pharmaceutical composition for treatment of HIV comprising one or more compounds of formula I.

Yet another aspect of the invention relates to a method of treating Human Immunodeficiency Virus comprising administering to a patient in need of such treatment a therapeutically effective amount of one or more compounds of formula I. A further aspect of the invention relates to a method of treating solid organ transplant rejection, graft v. host disease, arthritis, rheumatoid arthritis, inflammatory bowel disease, atopic dermatitis, psoriasis, asthma, allergies or multiple sclerosis comprising administering to a patient in need of such treatment a therapeutically effective amount of one or more compounds of formula I.

Still another aspect of this invention relates to a method of treating Human Immuno-deficiency Virus comprising administering to a patient in need of such treatment the one or more compounds of formula I in combination with one or more antiviral or other agents useful in the treatment. A further aspect of this invention relates to a method of treating solid organ transplant rejection, graft v. host disease, arthritis, rheumatoid arthritis, inflammatory bowel disease, atopic dermatitis, psoriasis, asthma or allergies comprising administering to a patient in need of such treatment one or more compounds of formula I in combination with one or more antiviral or other agents useful in the treatment. The CCR5 and antiviral or other agents which are components of the combination can be administered in a single dosage or administered separately. A kit comprising separate dosage forms of the actives is also contemplated.

Non-limiting examples of such combination agents include nucleoside and nucleotide reverse transcriptase inhibitors ("NRTI's), non-nucleoside reverse transcriptase inhibitors ("NNRTI's), protease inhibitors ("PI's), other antiviral agents, anti-HIV therapy agents and the like.

The term "nucleoside and nucleotide reverse transcriptase inhibitors" as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR trade name from Glaxo- Wellcome Inc., Research Triangle, N.C. 27709; didanosine (ddI) available under the VIDEX trade name from Bristol-Myers Squibb Co., Princeton, N.J. 08543; zalcitabine (ddC) available under the HIVID trade name from Roche Pharmaceuticals, Nutley, N.J. 07110; stavudine (d4T) available under the ZERIT trademark from Bristol-Myers Squibb Co., Princeton, N.J. 08543; lamivudine (3TC) available under the EPIVIR trade name from Glaxo-Wellcome Research Triangle, N.C. 27709; abacavir (1592U89) disclosed in WO96/30025 and available under the ZIAGEN trademark from Glaxo-Wellcome Research Triangle, N.C. 27709; adefovir dipivoxil [bis(POM)-PMEA] available under the PREVON trade name from Gilead Sciences, Foster City, Calif. 94404; lobucavir (BMS-180194), a nucleoside reverse transcriptase inhibitor disclosed in EP-0358154 and EP-0736533 and under development by Bristol-Myers Squibb, Princeton, N.J. 08543; BCH-10652, a reverse transcriptase inhibitor (in the form of a racemic mixture of BCH-10618 and BCH-10619) under development by Biochem Pharma, Laval, Quebec H7V, 4A7, Canada; emitricitabine [(−)-FTC] licensed from Emory University under Emory Univ. U.S. Pat. No. 5,814,639 and under development by Triangle Pharmaceuticals, Durham, N.C. 27707; beta-L-FD4 (also called beta-L-D4C and named beta-L-2', 3'-dicleoxy-5-fluoro-cytidene) licensed by Yale University to Vion Pharmaceuticals, New Haven Conn. 06511; DAPD, the purine nucleoside, (−)-beta-D-2,6,-diamino-purine dioxolane disclosed in EP 0656778 and licensed by Emory University and the University of Georgia to Triangle Pharmaceuticals, Durham, N.C. 27707; and lodenosine (FddA), 9-(2,3-dideoxy-2-fluoro-b-D-threo-pentofuranosyl)adenine, an acid stable purine-based reverse transcriptase inhibitor discovered by the NIH and under development by U.S. Bioscience Inc., West Conshohocken, Pa. 19428.

The term "non-nucleoside reverse transcriptase inhibitors" as used herein means non-nucleosides that inhibit the activity of HIV-1 reverse transcriptase.

Typical suitable NNRTIs include nevirapine (BI-RG-587) available under the VIRAMUNE trade name from Boehringer Ingelheim, the manufacturer for Roxane Laboratories, Columbus, Ohio 43216; delaviradine (BHAP, U-90152) available under the RESCRIPTOR trade name from Pharmacia & Upjohn Co., Bridgewater N.J. 08807; efavirenz (DMP-266) a benzoxazin-2-one disclosed in WO94/03440 and available under the SUSTIVA trade name from DuPont Pharmaceutical Co., Wilmington, Del. 19880-0723; PNU-142721, a furopyridine-thio-pyrimide under development by Pharmacia and Upjohn, Bridgewater N.J. 08807; AG-1549 (formerly Shionogi # S-1153); 5-(3,5-dichlorophenyl)-thio-4-isopropyl-1-(4-pyridyl)methyl-IH-imidazol-2-ylmethyl carbonate disclosed in WO 96/10019 and under clinical development by Agouron Pharmaceuticals, Inc., LaJolla Calif. 92037-1020; MKC442 (1-(ethoxy-methyl)-5-(1-methylethyl)-6-(phenylmethyl)-(2,4(1H,3H)-pyrimidinedione) discovered by Mitsubishi Chemical Co. and under development by Triangle Pharmaceuticals, Durham, N.C. 27707; and (+)-calanolide A (NSC-675451) and B, coumarin derivatives disclosed in NIH U.S. Pat. No. 5,489,697, licensed to Med Chem Research, which is co-developing (+) calanolide A with Vita-Invest as an orally administrable product.

The term "protease inhibitor" as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN(available from Merck) as well as nonpeptide protease inhibitors e.g., VIRACEPT (available from Agouron).

Typical suitable PIs include saquinavir (Ro 31-8959) available in hard gel capsules under the INVIRASE trade name and as soft gel capsules under the FORTOVASE trade name from Roche Pharmaceuticals, Nutley, N.J. 07110-1199; ritonavir (ABT-538) available under the NORVIR trade name from Abbott Laboratories, Abbott Park, Ill. 60064; indinavir (MK-639) available under the CRIXIVAN trade name from Merck & Co., Inc., West Point, Pa. 19486-0004; nelfnavir (AG-1343) available under the VIRACEPT trade name from Agouron Pharmaceuticals, Inc., LaJolla Calif. 92037-1020; amprenavir (141W94), trade name AGENERASE, a non-peptide protease inhibitor under development by Vertex Pharmaceuticals, Inc., Cambridge, Mass. 02139-4211 and available from Glaxo-Wellcome, Research Triangle, N.C. under an expanded access program; lasinavir (BMS-234475) available from Bristol-Myers Squibb, Princeton, N.J. 08543 (originally discovered by Novartis, Basel, Switzerland (CGP-61755); DMP-450, a cyclic urea discovered by Dupont and under development by Triangle Pharmaceuticals; BMS-2322623, an azapeptide under development by Bristol-Myers Squibb, Princeton, N.J. 08543, as a 2nd-generation HIV-1 PI; ABT-378 under development by Abbott, Abbott Park, Ill. 60064; and AG-1549 an orally active imidazole carbamate discovered by Shionogi (Shionogi #S-1153) and under development by Agouron Pharmaceuticals, Inc., LaJolla Calif. 92037-1020.

Other antiviral agents include hydroxyurea, ribavirin, IL-2, IL-12, pentafuside and Yissum Project No. 11607. Hydroyurea (Droxia), a ribonucleoside triphosphate reductase inhibitor, the enzyme involved in the activation of T-cells, was discovered at the NCl and is under development by Bristol-Myers Squibb; in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE 33653, 4530787, 4569790, 4604377, 4748234, 4752585, and 4949314, and is available under the PROLEUKIN (aldesleukin) trade name from Chiron Corp., Emeryville, Calif. 94608-2997 as a lyophilized powder for IV infusion or sc administration upon reconstitution and dilution with water; a dose of about 1 to about 20 million IU/day, sc is preferred; a dose of about 15 million IU/day, sc is more preferred. IL-12 is disclosed in WO96/25171 and is available from Roche Pharmaceuticals, Nutley, N.J. 07110-1199 and American Home Products, Madison, N.J. 07940; a dose of about 0.5 microgram/kg/day to about 10 microgram/kg/day, sc is preferred. Pentafuside (DP-178, T-20) a 36-amino acid synthetic peptide, disclosed in U.S. Pat. No. 5,464,933 licensed from Duke University to Trimeris which is developing pentafuside in collaboration with Duke University; pentafuside acts by inhibiting fusion of HIV-1 to target membranes. Pentafuside (3-100 mg/day) is given as a continuous sc infusion or injection together with efavirenz and 2 PI's to HIV-1 positive patients refractory to a triple combination therapy; use of 100 mg/day is preferred. Yissum Project No. 11607, a synthetic protein based on the HIV -1 Vif protein, is under preclinical development by Yissum Research Development Co., Jerusalem 91042, Israel. Ribavirin, 1-β-D-ribofuranosyl-1H-1,2,4-triazole-3-carboxamide, is available from ICN Pharmaceuticals, Inc., Costa Mesa, Calif.; its manufacture and formulation are described in U.S. Pat. No. 4,211,771.

The term "anti-HIV-1 therapy" as used herein means any anti-HIV-1 drug found useful for treating HIV-1 infections in man alone, or as part of multidrug combination therapies, especially the HAART triple and quadruple combination therapies. Typical suitable known anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from NNRTIs and PIs. Typical suitable HAART—multidrug combination therapies include:

(a) triple combination therapies such as two NRTIs and one PI; or (b) two NRTIs and one NNRTI ; and (c) quadruple combination therapies such as two NRTIs , one PI and a second PI or one NNRTI. In treatment of naive patients, it is preferred to start anti-HIV-1 treatment with the triple combination therapy; the use of two NRTIs and one PI is preferred unless there is intolerance to PIs. Drug compliance is essential. The CD4+ and HIV-1-RNA plasma levels should be monitored every 3-6 months. Should viral load plateau, a fourth drug, e.g., one PI or one NNRTI could be added. See the table below wherein typical therapies are further described:

Anti-HIV-1 Multi Drug Combination Therapies

A. Triple Combination Therapies
1. Two NRTIs[1]+one PI[2]
2. Two NRTIs[1]+one NNRTI[3]
B. Quadruple Combination Therapies[4]
  Two NRTIs+one PI+a second PI or one NNRTI
C. Alternatives:[5]
  Two NRTI[1]
  One NRTI[5]+one PI[2]
  Two PIs[6]+one NRTI[7] or NNRTI[3]
  One PI[2]+one NRTI[7]+one NNRTI[3]

Footnotes to Table

1. One of the following: zidovudine+lamivudine; zidovudine+didanosine; stavudine+lamivudine; stavudine+didanosine; zidovudine+zalcitabine
2. Indinavir, nelfinavir, ritonavir or saquinavir soft gel capsules.
3. Nevirapine or delavirdine.
4. See A-M. Vandamne et al Antiviral Chemistry & Chemotherapy 9:187 at p. 193-197 and FIGS. 1+2.
5. Alternative regimens are for patients unable to take a recommended regimen because of compliance problems or toxicity, and for those who fail or relapse on a recommended regimen. Double nucleoside combinations may lead to HIV-resistance and clinical failure in many patients.
6. Most data obtained with saquinavir and ritonavir (each 400 mg bid).
7. Zidovudine, stavudine or didanosine.

Another embodiment of the invention discloses the following compounds in Table 1. Table 1 also provides the mass spectral data (HRMS for the compounds.

TABLE 1

| Structure | HRMS |
|---|---|
| 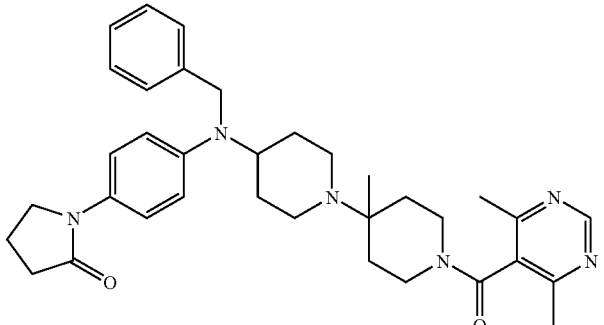 | 581.3595 |
| 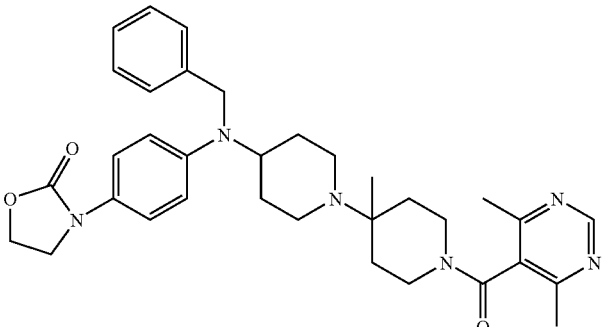 | 583.3389 |

TABLE 1-continued
| Structure | HRMS |
|---|---|
| 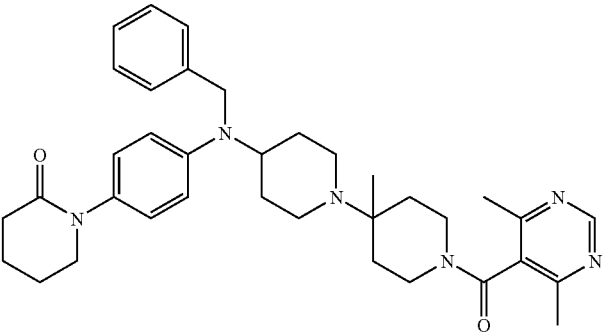 | 595.3766 |
| 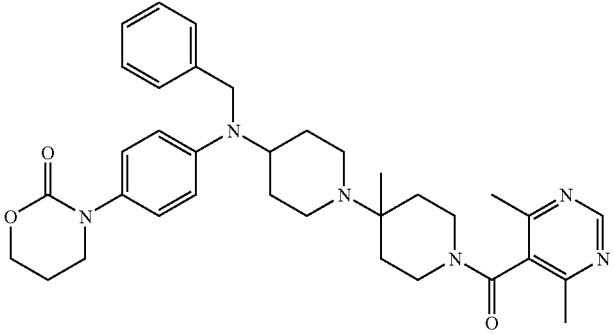 | 597.3555 |
| 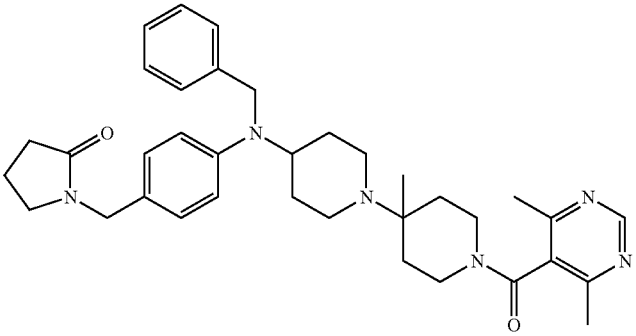 | 595.3754 |
| 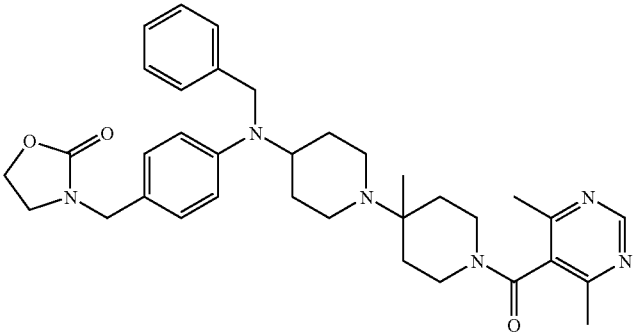 | 597.3543 |

TABLE 1-continued

| Structure | HRMS |
|---|---|
| 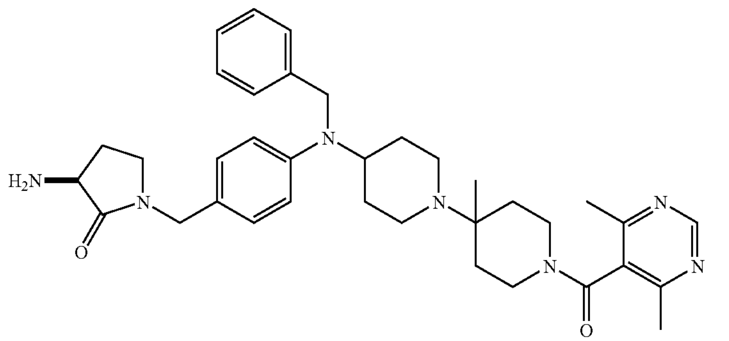 | 610.3886 |
| 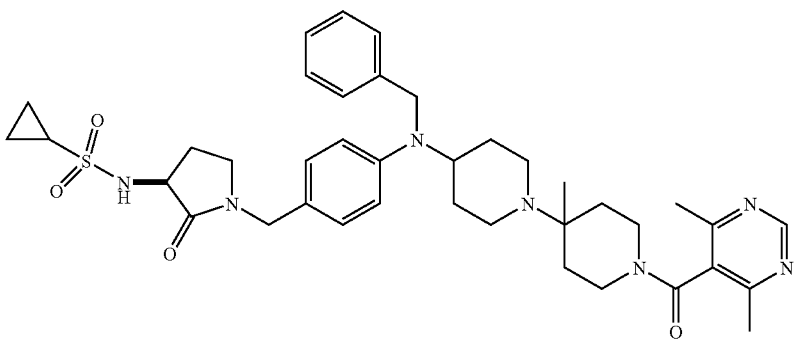 | 714.3835 |
| 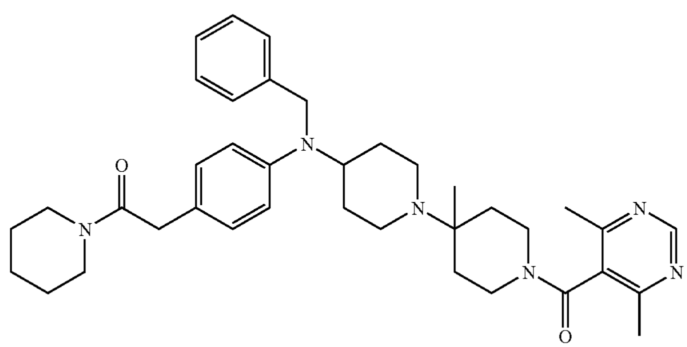 | 623.4065 |
| 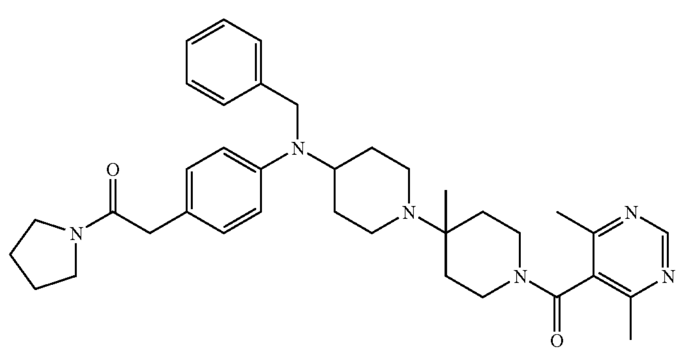 | 609.3925 |

TABLE 1-continued
| Structure | HRMS |
|---|---|
| 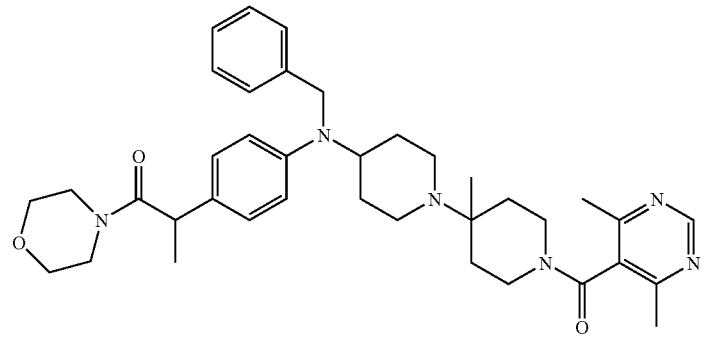 | 639.4013 |
| 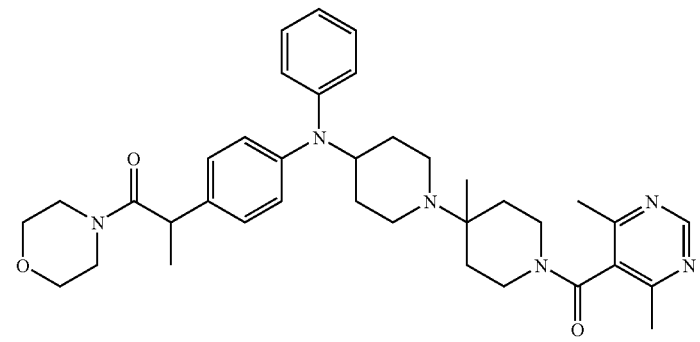 | 625.3875 |
| 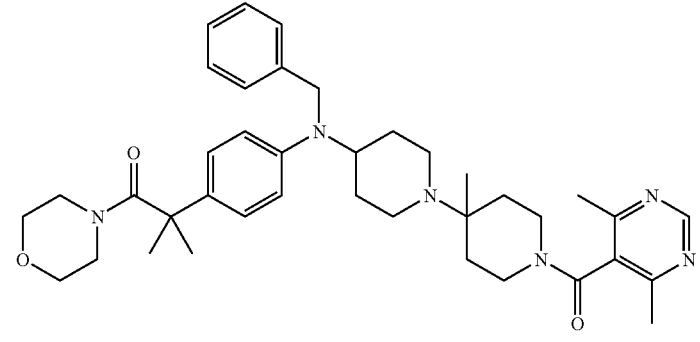 | 653.4186 |
| 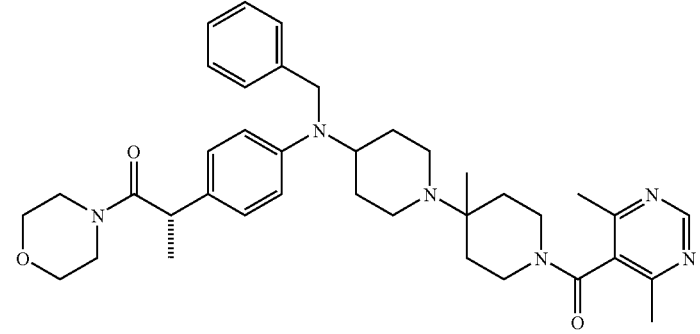 | 639.4019 |

TABLE 1-continued
| Structure | HRMS |
|---|---|
| 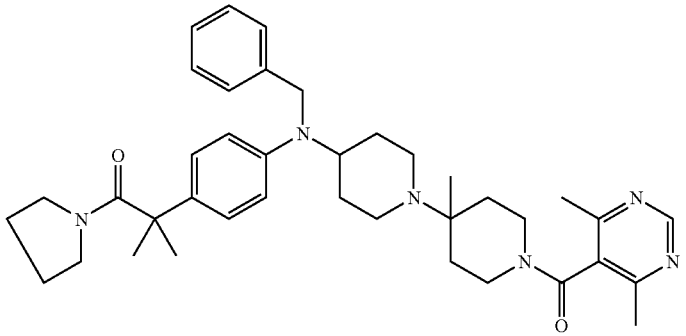 | 637.4232 |
| 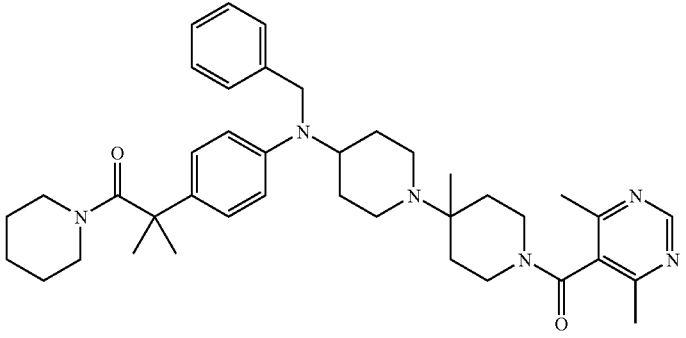 | 651.4383 |
| 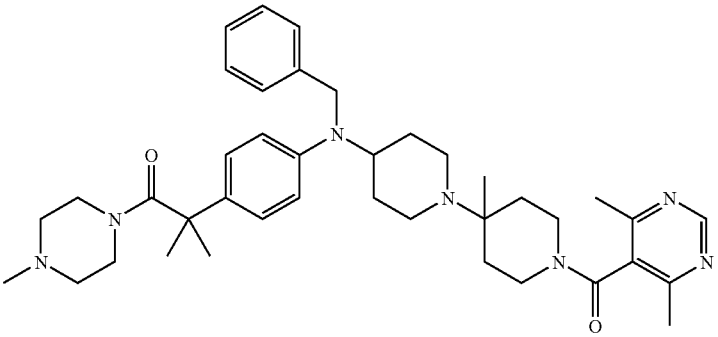 | 666.4473 |
| 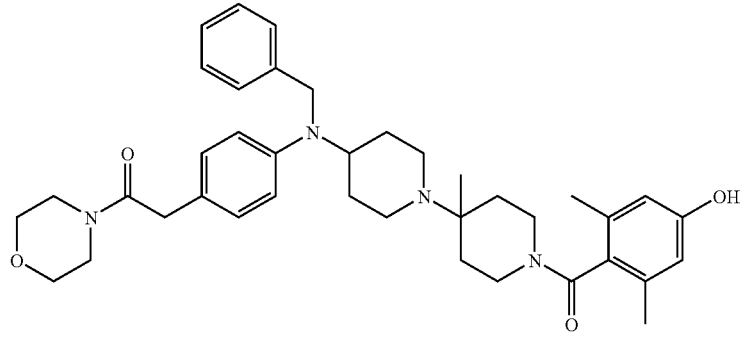 | 639.3892 |

TABLE 1-continued

| Structure | HRMS |
|---|---|
| 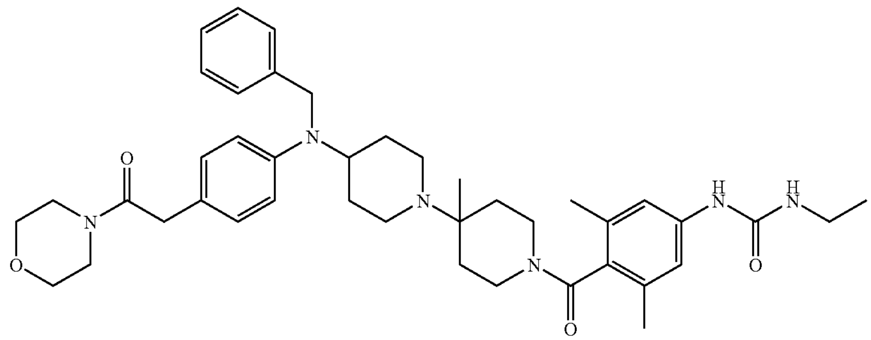 | 709.4434 |
| 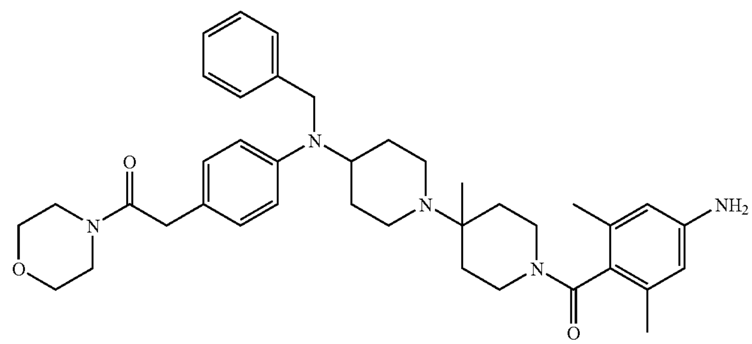 | 638.4064 |
| 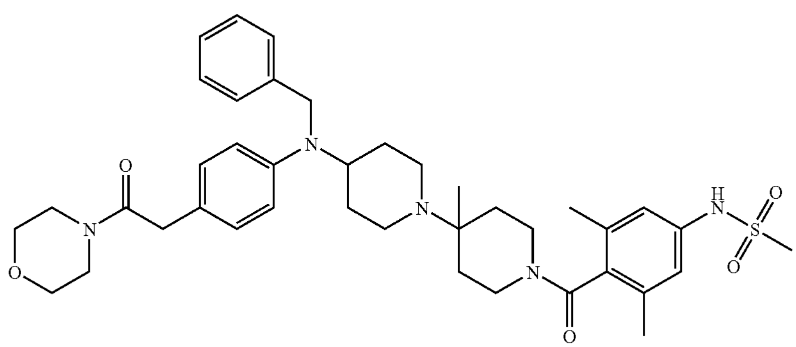 | 716.3818 |
| 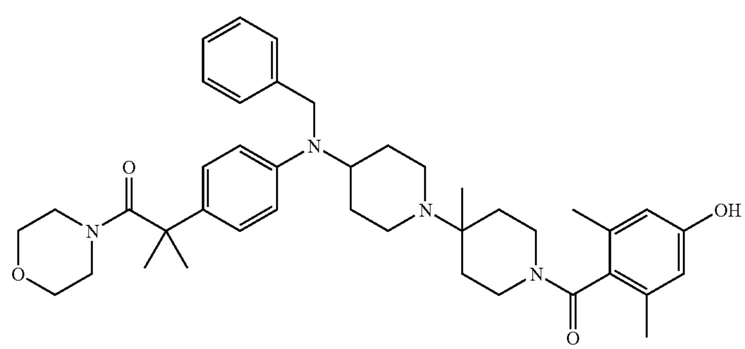 | 667.4194 |

TABLE 1-continued

| Structure | HRMS |
|---|---|
| 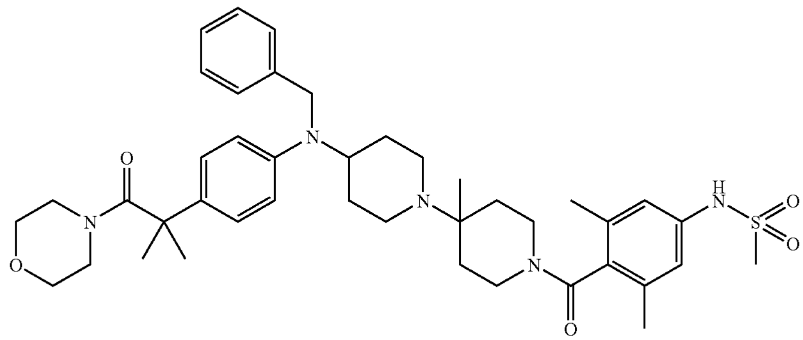 | 744.4169 |
| 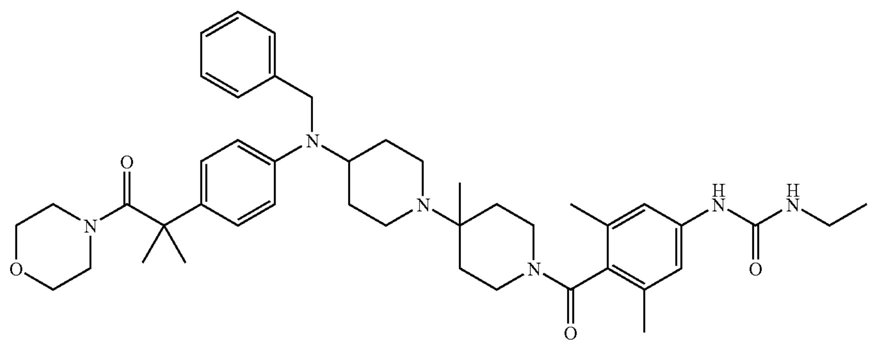 | 737.4759 |
| 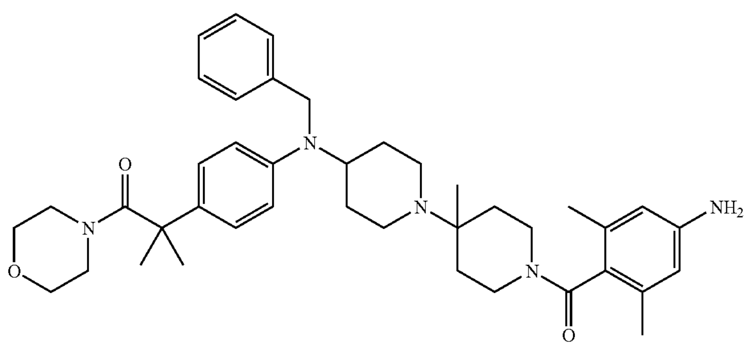 | 666.4389 |
| 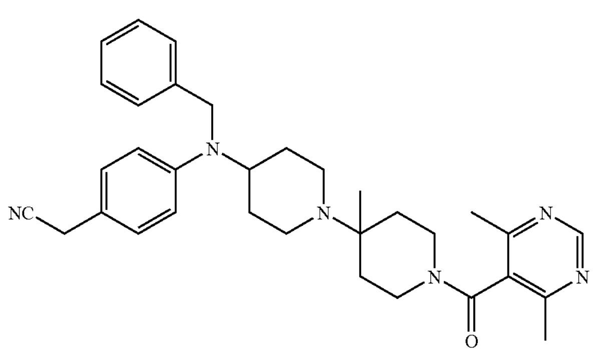 | 537.3335 |

TABLE 1-continued
| Structure | HRMS |
|---|---|
| 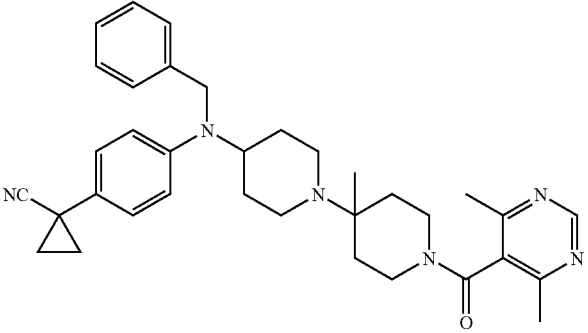 | 563.3495 |
| 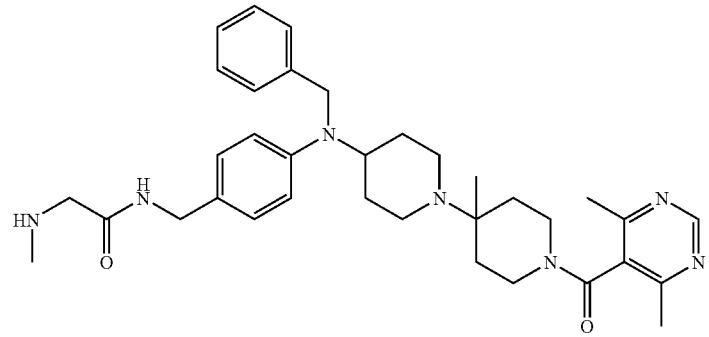 | 598.3856 |
| 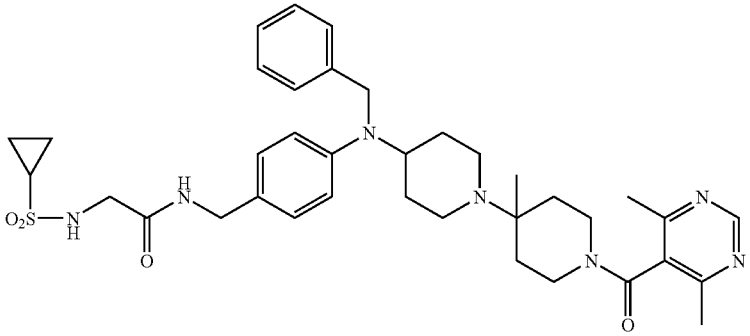 | 688.3638 |
| 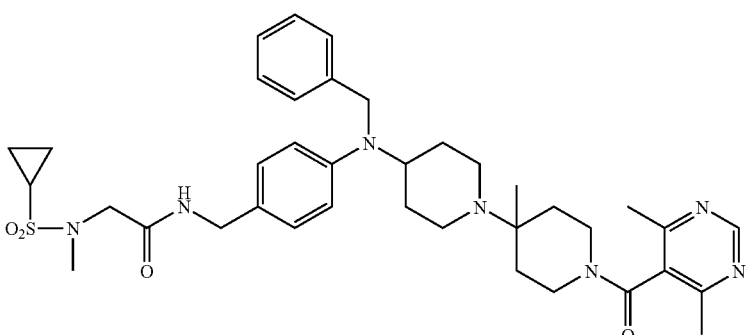 | 702.3740 |

TABLE 1-continued
| Structure | HRMS |
|---|---|
| 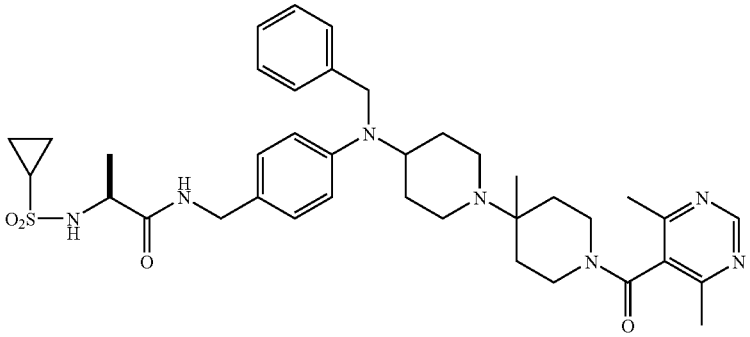 | 702.3790 |
| 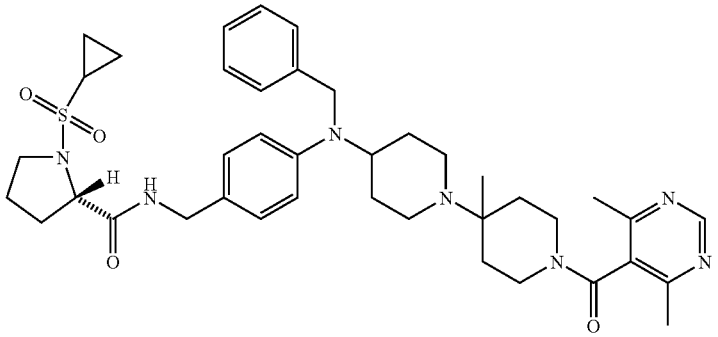 | 728.3965 |
| 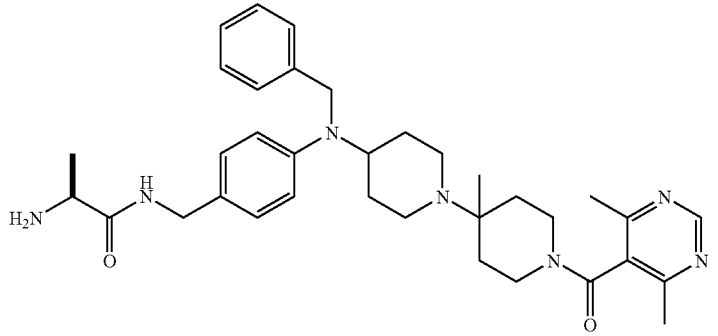 | 598.3868 |
| 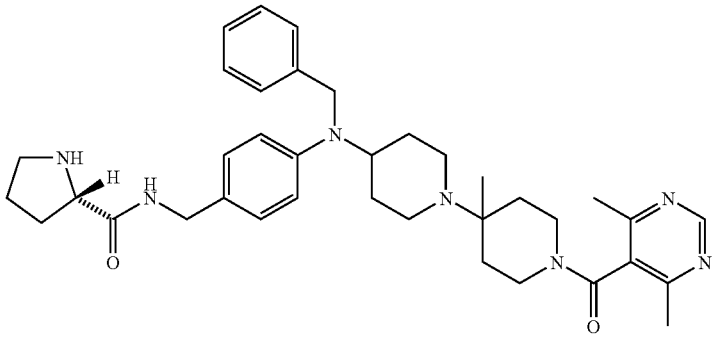 | 624.4031 |

TABLE 1-continued
| Structure | HRMS |
|---|---|
| 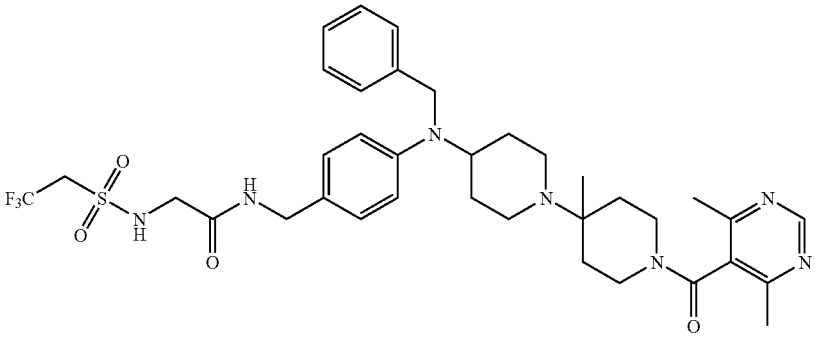 | 673.3421 |
| 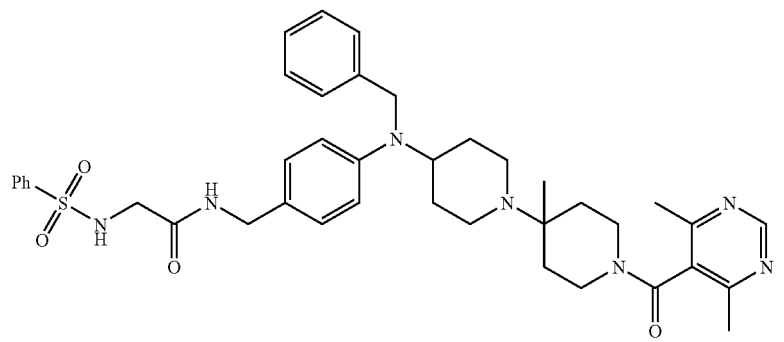 | 724.3638 |
| 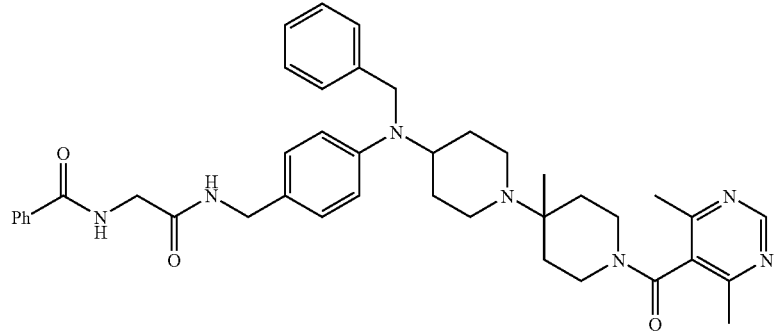 | 688.3962 |
| 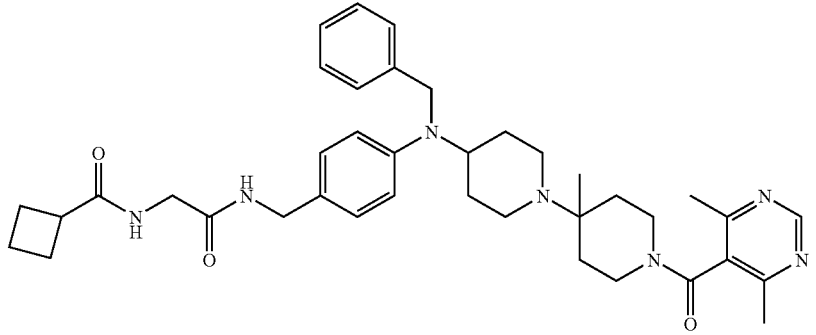 | 666.4124 |

TABLE 1-continued
| Structure | HRMS |
|---|---|
| 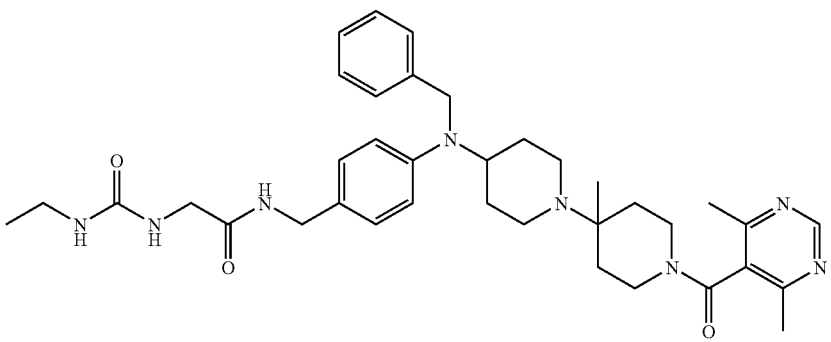 | 655.4097 |
| 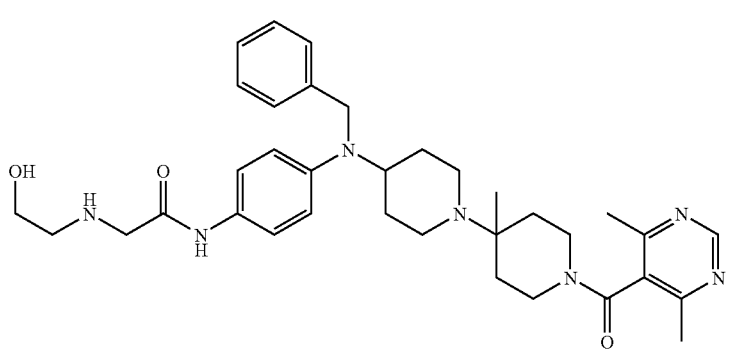 | 614.3826 |
| 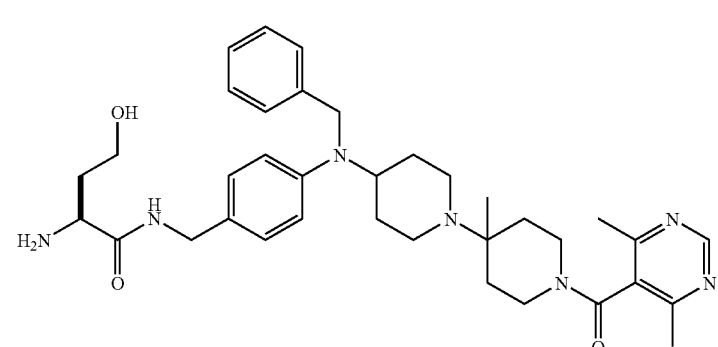 | 728.4503 |
| 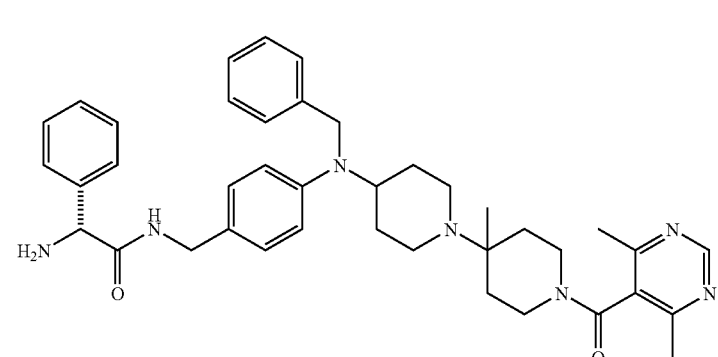 | 660.4025 |

TABLE 1-continued
| Structure | HRMS |
|---|---|
| 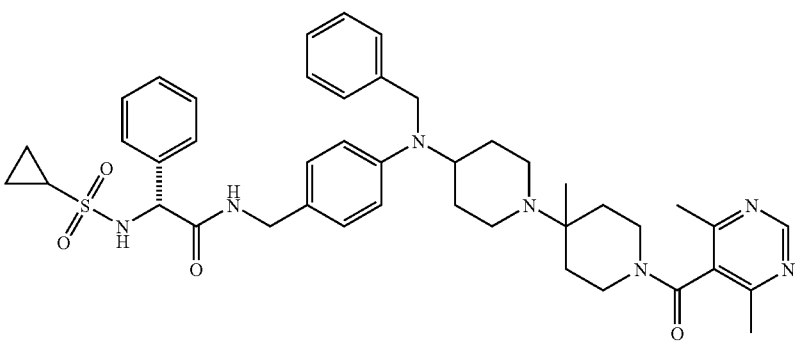 | 764.3951 |
| 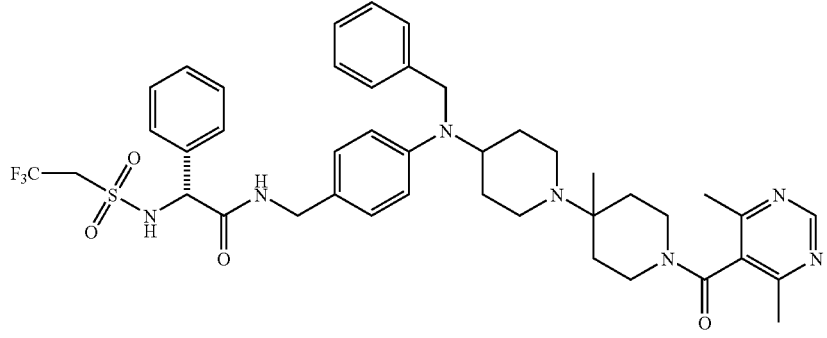 | 806.3659 |
| 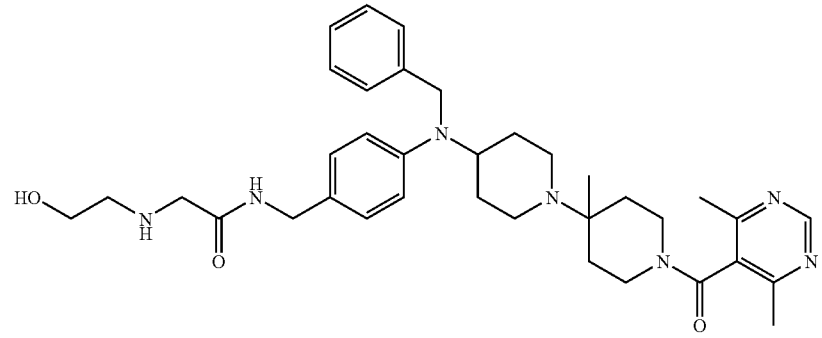 | 628.3998 |
| 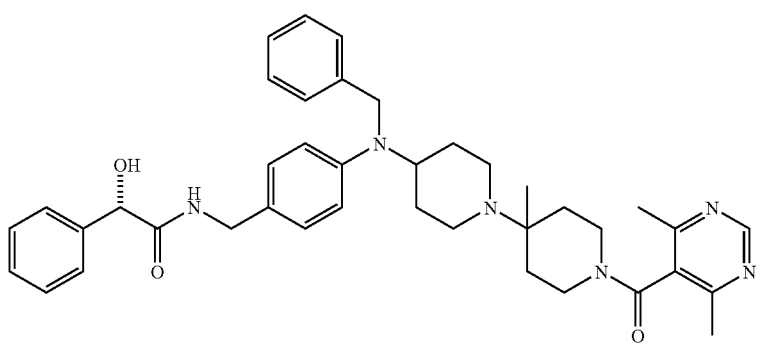 | 661.3885 |

TABLE 1-continued
| Structure | HRMS |
|---|---|
| 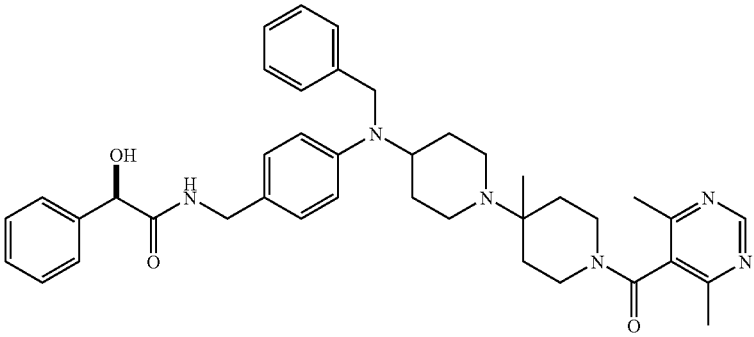 | 661.3885 |
| 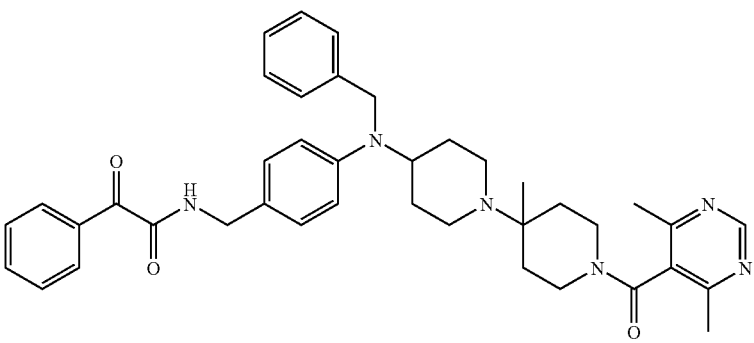 | 659.3725 |
| 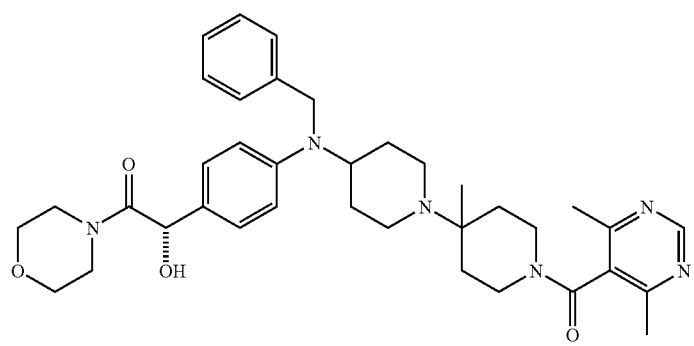 | 6414.3833 |
| 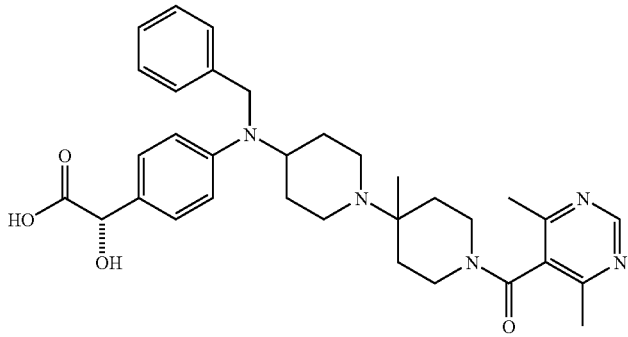 | |

TABLE 1-continued
| Structure | HRMS |
|---|---|
| 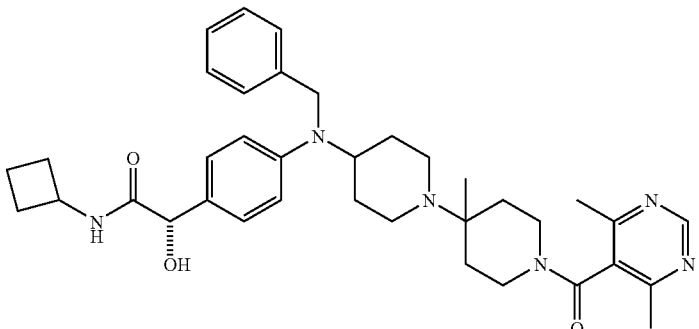 | 625.3827 |
| 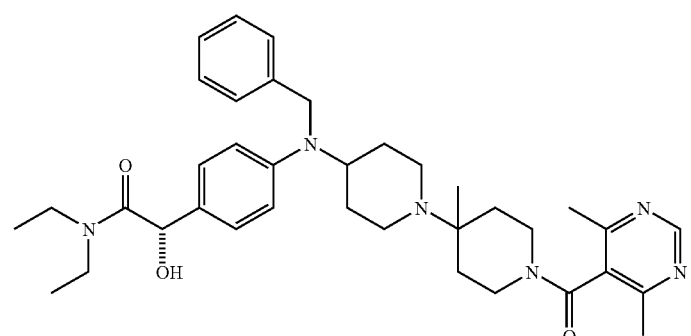 | 627.4033 |
| 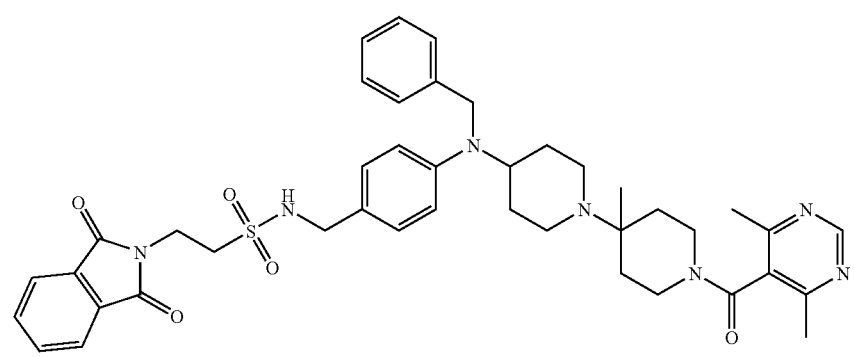 | 764.3587 |
| 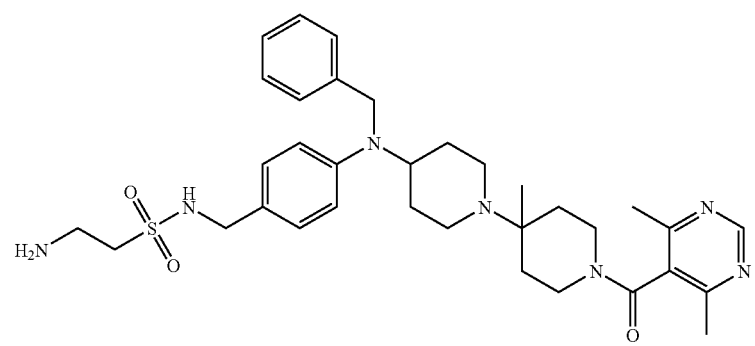 | 634.3534 |

TABLE 1-continued
| Structure | HRMS |
|---|---|
| 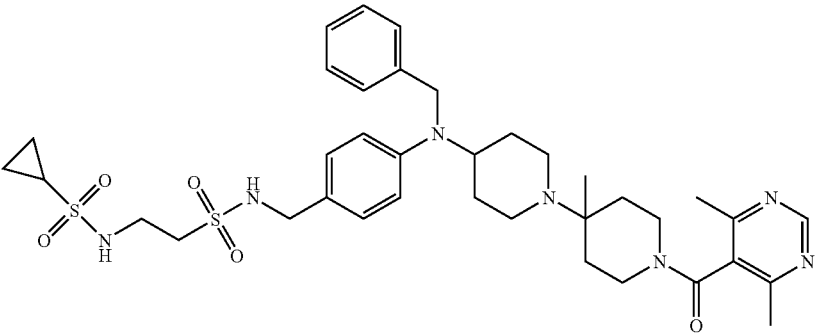 | 738.3482 |
| 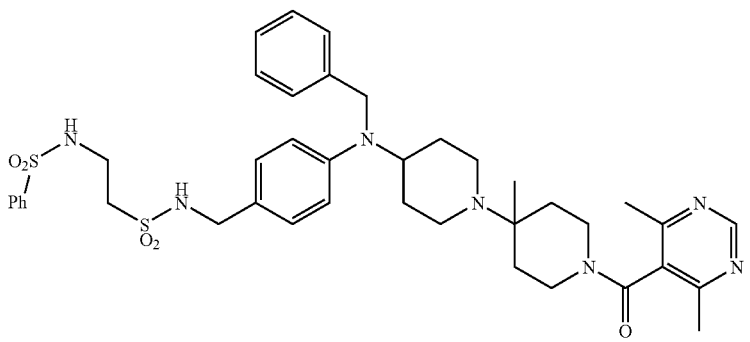 | 774.3481 |
| 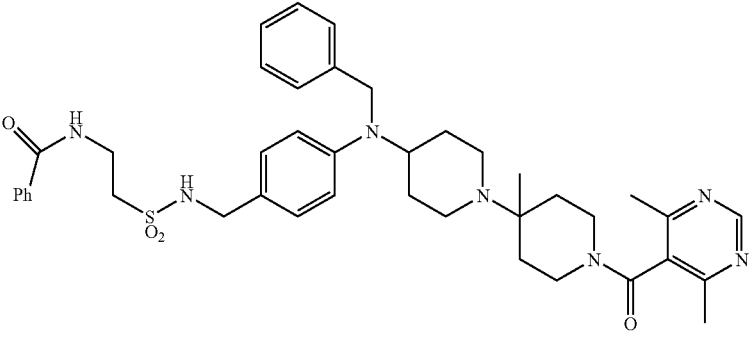 | 738.3814 |
| 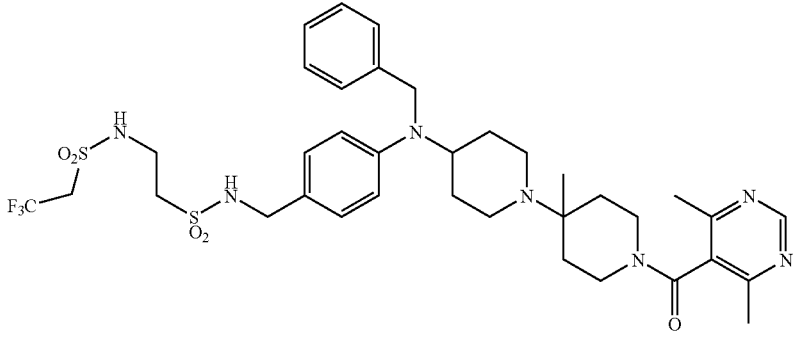 | 780.3192 |

TABLE 1-continued
| Structure | HRMS |
|---|---|
| 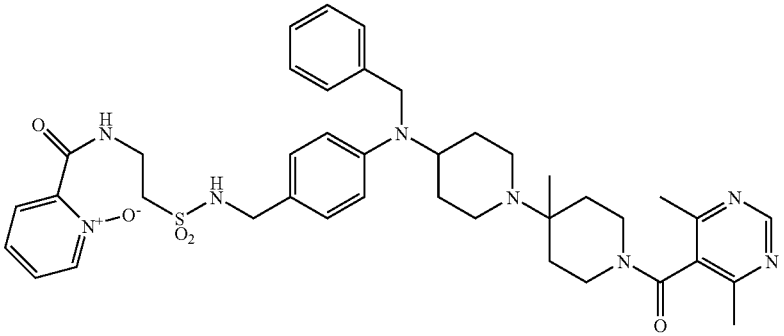 | 755.3714 |
| 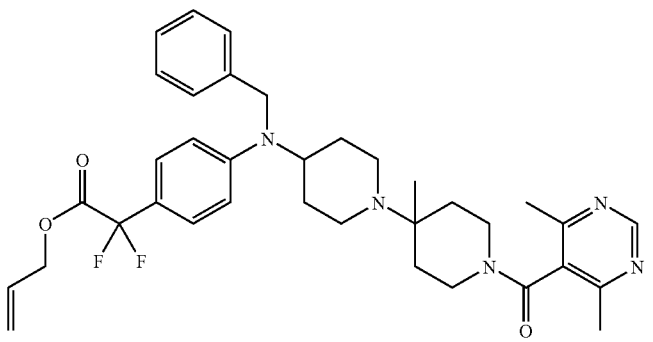 | 632.3442 |
| 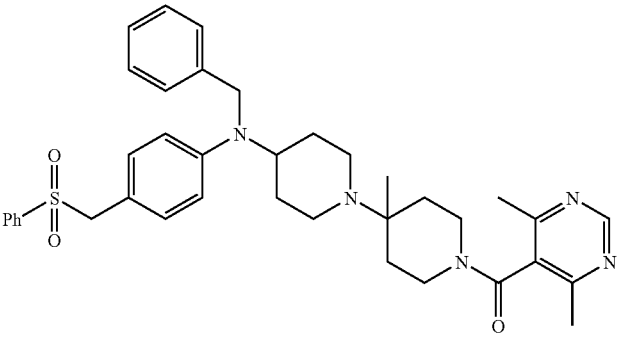 | 652.3336 |
| 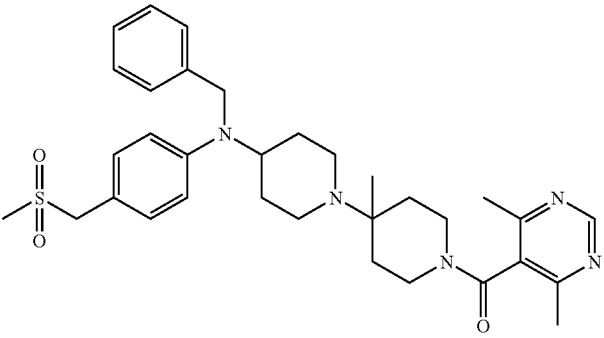 | 590.3187 |

TABLE 1-continued
| Structure | HRMS |
|---|---|
| 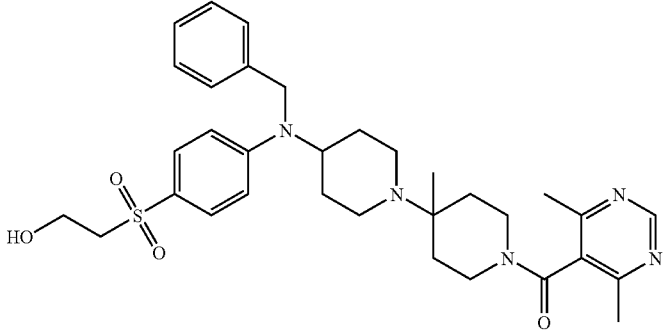 | 606.3103 |
| 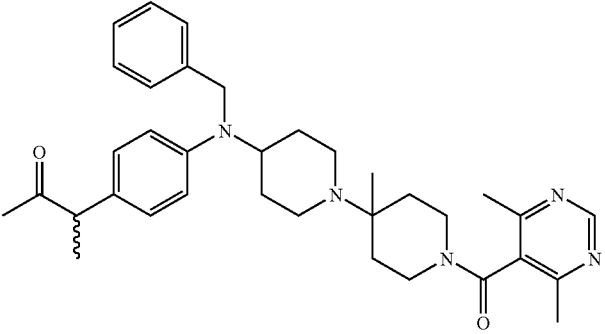 | 568.3666 |
| 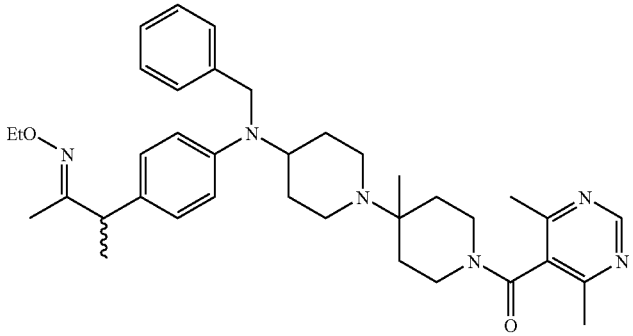 | 611.4089 |
| 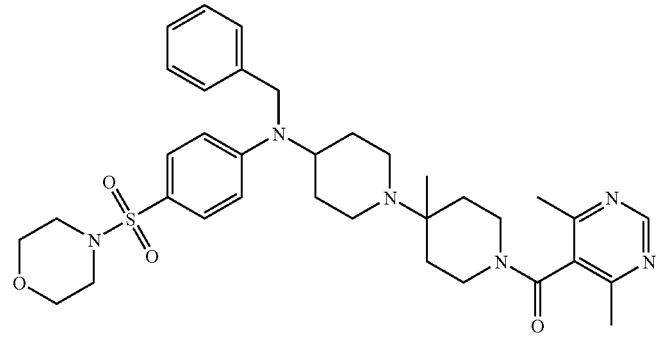 | 647.3378 |

TABLE 1-continued
| Structure | HRMS |
|---|---|
| 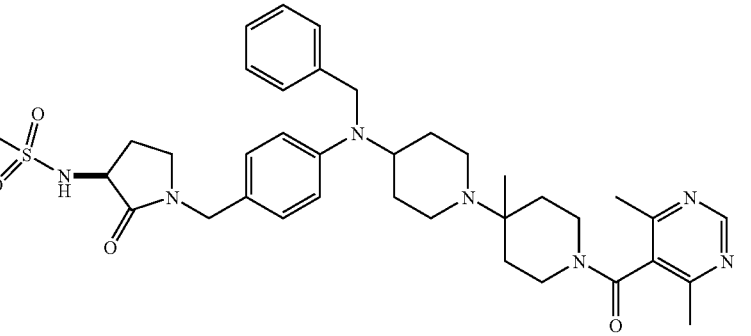 | 529.3269 |
Yet another embodiment of the present invention discloses the following compounds in Table 2. Table 2 additionally provides the activity data (IC$_{50}$ in nanomolar, nM) for the compounds listed therein, as determined by the Luciferase Replication assay detailed in a later section of this specification.
TABLE 2
| Structure | IC$_{50}$ (nM) |
|---|---|
| 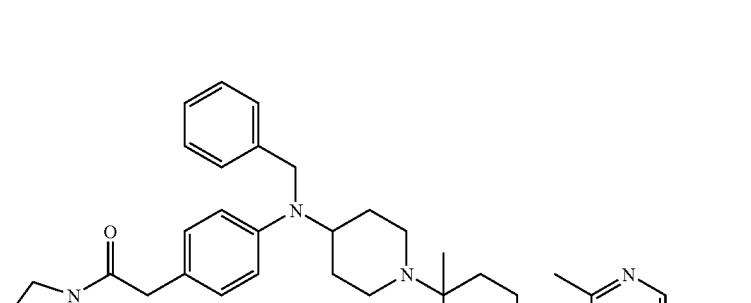 | 0.14 |
| 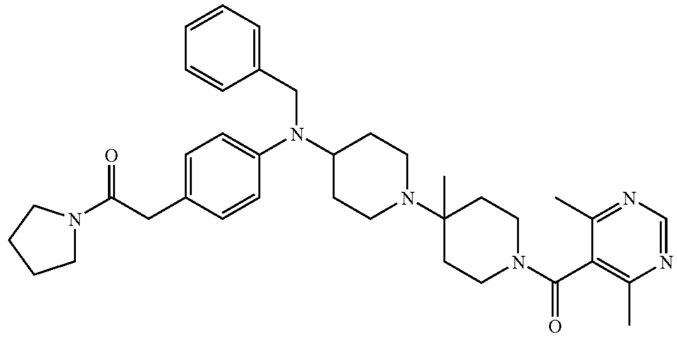 | 0.13 |

TABLE 2-continued
| Structure | IC$_{50}$ (nM) |
|---|---|
| 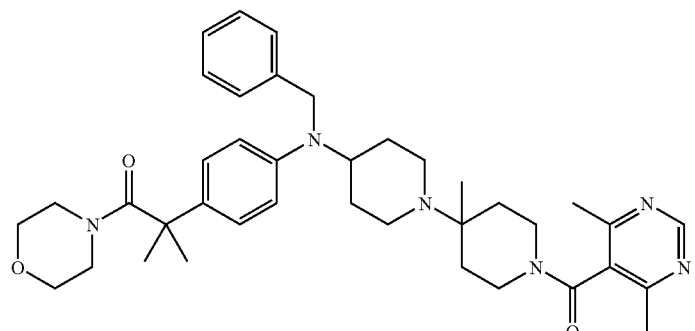 | 0.14 |
| 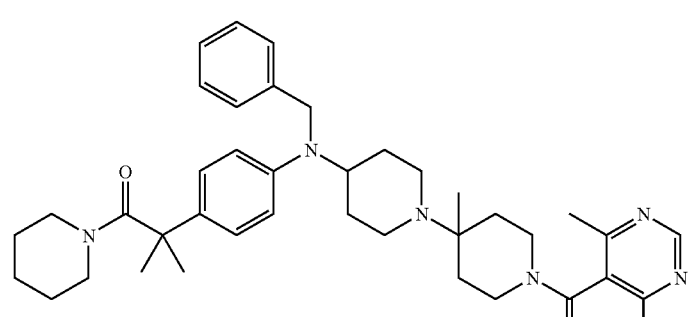 | 0.18 |
| 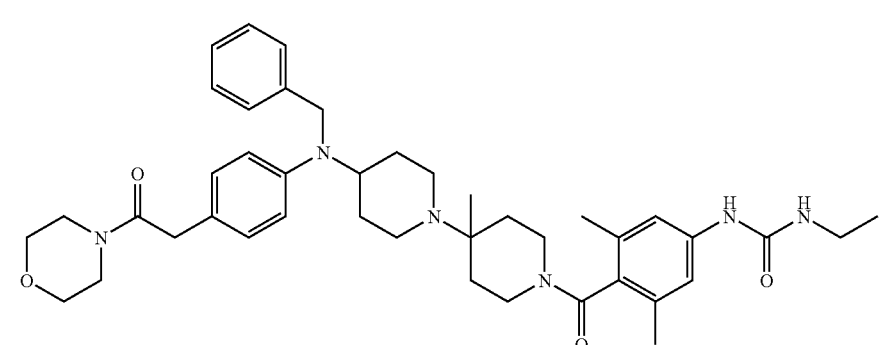 | 0.19 |
| 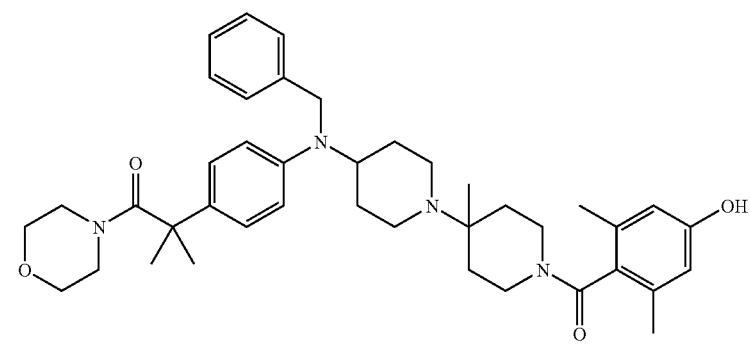 | <0.1 |

TABLE 2-continued

| Structure | IC$_{50}$ (nM) |
|---|---|
| 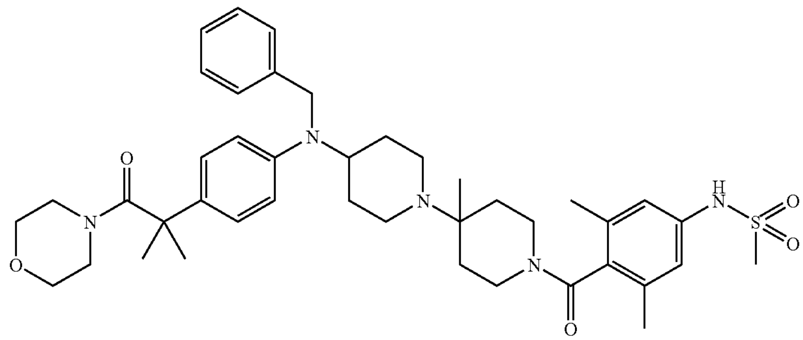 | 0.16 |
| 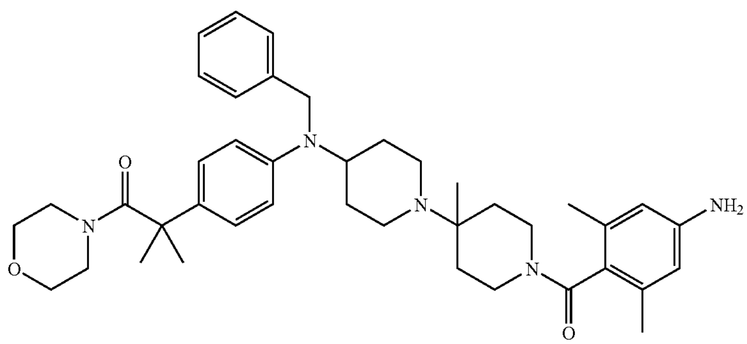 | 0.13 |
| 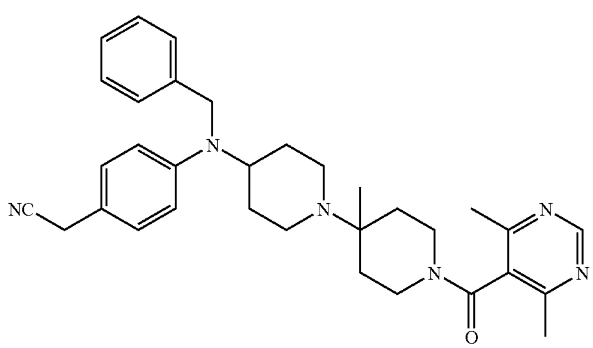 | 0.14 |
| 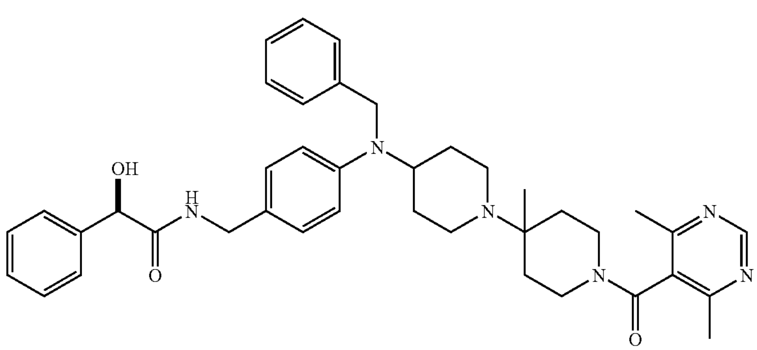 | 0.19 |

TABLE 2-continued

| Structure | IC$_{50}$ (nM) |
|---|---|
| 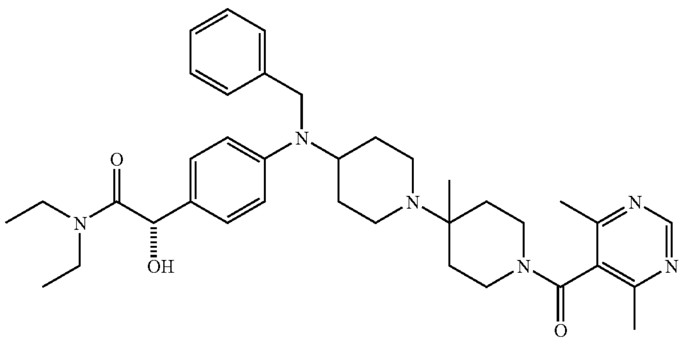 | 0.16 |
| 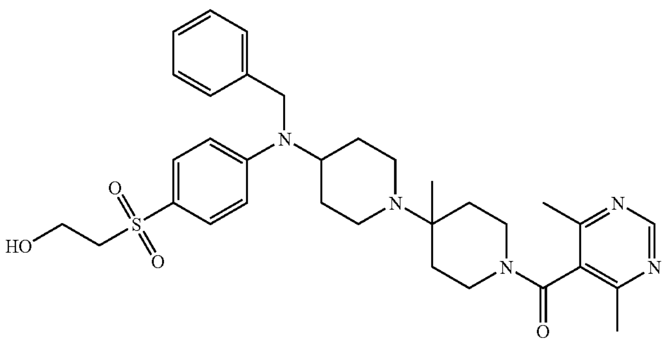 | 0.17 |
| 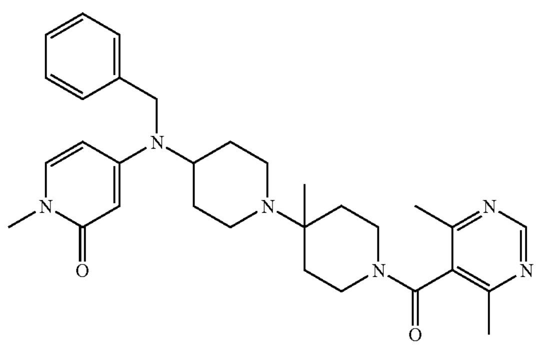 | 0.15 |

The compounds of the present invention, also referred to herein as the inventive compounds, are particularly useful as a CCR5 antagonist.

Compounds of the invention can be made by procedures known in the art, or by the methods described in the examples below. The following preparative schemes and examples should not be construed to limit the scope of the disclosure. Alternative mechanistic pathways and analogous structures within the scope of the invention may be apparent to those skilled in the art.

The following solvents and reagents may be referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxy-benzotriazole (HOBT); m-chloroperbenzoic acid (MCPBA); triethylamine (Et$_3$N); diethyl ether (Et$_2$O); tert-butoxy-carbonyl (BOC); 1,8-diazabicyclo[5.4.0]undec-7-ene (DBU); dimethyl-sulfoxide (DMSO); p-toluene sulfonic acid (p-TSA); potassium bis(trimethylsilyl)-amide (KHMDA); 4-dimethylaminopryidine (DMAP); N,N,N-diisopropylethylamine (DIPEA); Alloc: allyloxycarbamate; MeCN: acetonitrile; and 1-(3-dimethyl-aminopropyl)-3-ethyl carbodiimide hydrochloride (EDCl). RT is room temperature.

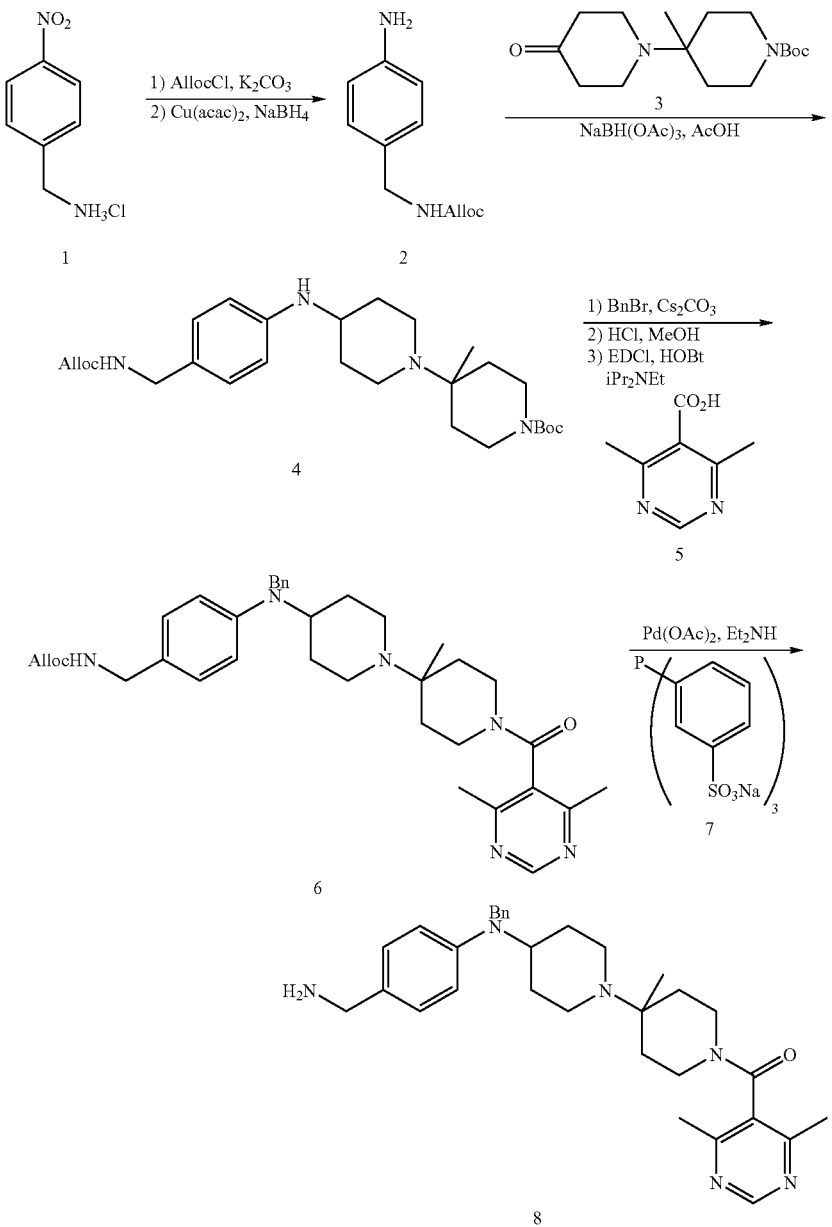

Scheme 1

EXAMPLE 1

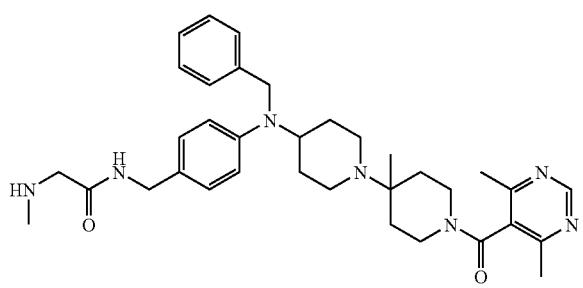

Step 1

To a solution of 4-nitrobenzyl amine hydrochloride 1 (7.5 g, 40 mmol) in 1:1 EtOAc/H$_2$O (120 mL) was added K$_2$CO$_3$ (16.5 g, 119 mmol) and allyl chloroformate (5.07 mL, 47.8 mmol). The resultant biphasic solution was stirred vigorously at room temperature for 16 hours. The aqueous layer was extracted with EtOAc (3×). The combined organic layers were washed with brine, dried over Na$_2$SO$_4$, filtered and concentrated to afford 15.3 g of the crude product which was used without further purification.

Step 2

To a slurry of copper(II) acetylacetonate (2.54 g, 9.7 mmol) in EtOH (70 mL) at 0° C. was slowly added sodium borohydride (4.71 g, 124.4 mmol). The resultant slurry was stirred at 0° C. for 30 min. A slurry of the nitro compound from step 1 (9.2 g, 38.9 mmol) in EtOH (70 mL) was added and the resultant solution was stirred at 0° C. and allowed to slowly warm to room temperature over 16 hours. Water (20 mL) was slowly added to the solution. The solution was then filtered through Celite and concentrated. The crude product was partitioned between water and CH$_2$Cl$_2$. The aqueous layer was extracted with CH$_2$Cl$_2$ (3×). The combined organic layers were dried over Na$_2$SO$_4$, filtered and concentrated to afford 6.8 g as a dark oil. The product was used without further purification.

Step 3

To a solution of the aniline from Step 2 (2.36 g, 11.4 mmol) in 1,2-dichloroethane (40 mL) was added the ketone 3 (3.4 g, 11.4 mmol, the preparation of this compound is disclosed in PCT Publication WO2003/020716, published on Mar. 13, 2003) and acetic acid (1.32 mL, 22.8 mmol) followed by sodium triacetoxyborohydride (7.27 g, 34.3 mmol). The resultant mixture was stirred at room temperature for 48 hours. Sodium hydroxide (1M, 40 mL) was added and the mixture was stirred at room temperature for 30 min. The aqueous layer was extracted with CH$_2$Cl$_2$ (3×). The combined organic layers were dried over Na$_2$SO$_4$, filtered and concentrated. The crude product was purified by flash chromatography (2:1 hexanes/acetone) to afford 4.0 g (72%) as a yellow oil.

Step 4

To a solution of the aniline from Step 3 (4.0 g, 8.2 mmol) in DMF (30 mL) was added benzyl bromide (2.93 mL, 24.6 mmol), Cs$_2$CO$_3$ (8.0 g, 24.6 mmol) and KI (544 mg, 3.28 mmol). The mixture was heated to 80° C. for 16 hours. The solution was cooled to RT and partitioned between water and EtOAc. The aqueous layer was extracted with EtOAc (3×). The combined organic layers were washed with brine, dried over Na$_2$SO$_4$, filtered and concentrated to afford 4.7 g as an orange oil. The product was used without further purification.

Step 5

To a solution of the Boc carbamate (from step 4) in CH$_2$Cl$_2$ (20 mL) was added 1,3 dimethoxy benzene (5 mL) followed by TFA (20 mL). The solution was stirred at room temp. for 4 hours. The solution was concentrated. The crude oil was partitioned between 1M HCl and Et$_2$O. The aqueous layer was extracted with Et$_2$O (2×). The aqueous layer was then adjusted to pH 10 with 3N NaOH. The aqueous layer was extracted with CH$_2$Cl$_2$ (4×). The combined organic layers were dried over Na$_2$SO$_4$, filtered and concentrated to afford 2.95 g as a yellow oil. The product was used without further purification.

Step 6

To a solution of the amine from step 5 (2.95 g, 6.2 mmol) was added EDCl (1.79 g, 9.3 mmol), the pyrimidine acid 5 (1.41 g, 9.3 mmol, described in U.S. Pat. No. 6,391,865), HOBt (1.26 g, 9.3 mmol) and iPr$_2$NEt (5.4 mL, 31 mmol). The resultant solution was stirred at room temperature for 16 hours. The solution was concentrated. The crude oil was partitioned between 1M NaOH and EtOAc. The aqueous layer was extracted with EtOAc (3×). The combined organic layers were washed with brine, dried over Na$_2$SO$_4$, filtered and concentrated. The crude product was purified by flash chromatography (gradient 2:1 to 4:1 Acetone/hexanes) to afford amide 6 2.0 g as a yellow foam (40% over 3 steps).

Step 7

To a solution of the allyl carbamate 6 (from Step 6) (1.05 g, 1.7 mmol) in 5:1 MeCN/water (60 mL) was added diethyl amine (3.5 mL, 34 mmol), 3,3',3"-phosphinidynetris(benzene-sulfonic acid trisodium salt (7)(39 mg, 0.068 mmol, available from Aldrich Chemical Company, Milwaukee, Wis.) and palladium(II) acetate (7.6 mg, 0.034 mmol). The mixture was allowed to stir at room temperature for 5 hours. The solution was concentrated to afford 900 mg amine 8 as a yellow oil. The amine was used without further purification.

Step 8

To a solution of the amine 8 from Step 7 (130 mg, 0.25 mmol) in MeCN (1 mL) was added EDCl (72 mg, 0.37 mmol), N-Boc sarcosine (70 mg, 0.37 mmol), HOBt (51 mg, 0.37 mmol) and iPr$_2$NEt (0.217 mL, 1.25 mmol). The resultant solution was stirred at room temperature for 16 hours. The solution was concentrated. The crude oil was partitioned between 1M NaOH and EtOAc. The aqueous layer was extracted with EtOAc (3×). The combined organic layers were washed with brine, dried over Na$_2$SO$_4$, filtered and concentrated. The crude product was purified by prep TLC (1:1 Acetone/hexanes) to afford 95 mg as a white foam (55%).

Step 9

To a solution of the t-butyl carbamate from step 8 (75 mg) in MeOH (2 mL) was added 4N HCl (2 mL, in dioxane). The solution was stirred at room temperature for 3 hours. The solution was concentrated to afford the amine as the HCl salt. HRMS calc for C$_{35}$H$_{48}$N$_7$O$_2$(MH$^+$): 598.3869; found: 598.3856.

EXAMPLE 2

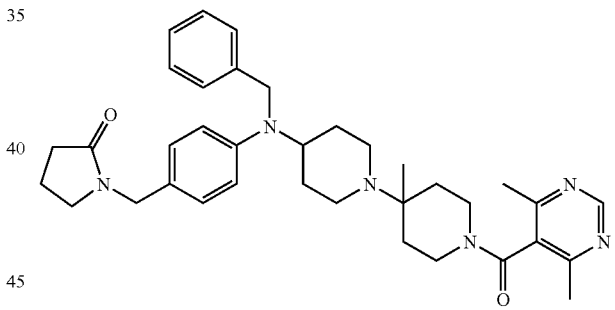

Step 1

To a solution of amine 8 (140 mg, 0.27 mmol) in CH$_2$Cl$_2$ (2 mL) at 0° C. was added Et$_3$N (0.036 mL, 0.27 mmol) and 4-chlorobutyryl chloride (0.030 mL, 0.27 mmol). The solution was allowed to stir at 0° C. for 30 min. then an additional 1 hour at room temp. The solution was diluted with CH$_2$Cl$_2$ and washed with NaHCO$_3$, dried over Na$_2$SO$_4$, filtered and concentrated. The crude product was redissolved in dry THF (2 mL). To this solution NaH (22 mg, 0.56 mmol) was added and the solution was heated to reflux for 6 hours. The solution was cooled to room temperature and water was slowly added. The aqueous layer was extracted with EtOAc (3×). The combined organic layers were washed with brine, dried over Na$_2$SO$_4$, filtered and concentrated. The crude product was purified by prep TLC (1:1 Acetone/hexanes) to afford 32 mg as a white foam (20%). The HCl salt of this product was formed by the addition of 4N HCl (dioxane) followed by evaporation. HRMS calc for C$_{36}$H$_{47}$N$_6$O$_2$(MH$^+$): 595.3761; found: 595.3754.

EXAMPLE 3

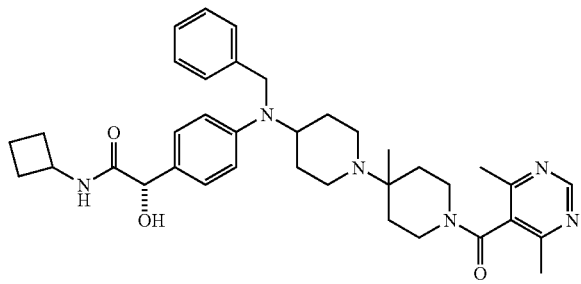

Step 1

To a solution of ethyl (S)-mandelate (10.0 g, 55 mmol) in CH₂Cl₂ (300 mL) was added DMAP (670 mg, 5.5 mmol), acetic anhydride (5.77 mL, 61 mmol) and iPr₂NEt (10.6 mL, 61 mmol). The solution was stirred at room temperature for 16 hours. The solution was diluted with CH₂Cl₂ and washed with NH₄Cl (aq.). The organic layer was dried over Na₂SO₄, filtered and concentrated to afford 12.0 g as a clear oil. The product was used without further purification.

Step 2

To a solution of the arene from Step 1 (12 g, 54.1 mmol) in acetic anhydride (65 mL) at 0° C. was added dropwise a mixture of nitric acid (13 mL) and sulfuric acid (15 mL). The solution was stirred at 0° C. for 4 hours. The solution was slowly poured into water and extracted with EtOAc. The organic layer was washed with sat. NaHCO₃ and brine. The organic layer was dried over Na₂SO₄, filtered and concentrated. The crude product was purified by flash chromatography (gradient 100:0 to 7:3 hex/EtOAc) to afford the desired nitro product (9.5 g) as a 3:1 (para:meta) inseparable mixture of nitro regioisomers.

Step 3

To a solution of the nitro compound from step 2 (9.5 g, 35.6 mmol) in EtOH (100 mL) was added H₂SO₄ (20 drops). The resultant solution was heated to reflux for 16 hours. The solution was concentrated. The crude product was partitioned between water and EtOAc. The aqueous layer was extracted with EtOAc (3×). The combined organic layers were washed with brine, dried over Na₂SO₄, filtered and concentrated to afford 6.6 g of the alcohol as a yellow oil. The desired para nitro compound was isolated via recrystallization from hexanes/diethyl ether.

Step 4

To a solution of the alcohol (3.6 g, 16 mmol) from step 3 in DMF (10 mL) was added t-butyldimethylsilyl chloride (4.8 g, 32 mmol) and imidazole (4.4 g, 64 mmol). The solution was stirred at room temperature for 16 hours. The solution was diluted with water and extracted with EtOAc (3×). The combined organic layers were washed with brine, dried over Na₂SO₄, filtered and concentrated. The crude product was purified by flash chromatography (gradient 100:0-85:15 hex:EtOAc) to afford 5.0 g (92%) of the silyl ether as a clear oil.

Step 5

To a slurry of copper(II) acetylacetonate (962 mg, 3.67 mmol) in EtOH (80 mL) at 0° C. was slowly added sodium borohydride (1.67 g, 44.1 mmol). The resultant slurry was stirred at 0° C. for 30 min. A slurry of the nitro compound from step 4 (5.0 g, 14.7 mmol) in EtOH (80 mL) was added and the resultant solution was stirred at 0° C. and allowed to slowly warm to room temperature for 2.5 hours. Water (10 mL) was slowly added to the solution. The solution was then filtered through Celite and concentrated. The crude product was partitioned between water and CH₂Cl₂. The aqueous layer was extracted with CH₂Cl₂ (3×). The combined organic layers were dried over Na₂SO₄, filtered and concentrated to afford 4.24 g of the aniline as a dark oil. The product was used without further purification.

Step 6

The aniline from step 5 (4.24 g, 13.7 mmol) in 1,2-dichloroethane (75 mL) was treated with ketone 3 (4.07 g, 13.7 mmol) and acetic acid (1.34 mL, 23.3 mmol) followed by sodium triacetoxyborohydride (7.26 g, 34.3 mmol) under the conditions described in step 3 example 1. The crude product was purified by flash chromatography (gradient 9:1 to 1:3 hexanes/EtOAc) to afford 4.2 g (52%) of the aniline as a yellow oil.

Step 7

To a solution of the aniline from step 6 (4.2 g, 7.1 mmol) in DMF (50 mL) was added benzyl bromide (2.56 mL, 21.4 mmol), Cs₂CO₃ (6.97 g, 21.4 mmol) and potassium iodide (236 mg, 1.42 mmol). The mixture was heated to 75° C. for 16 hours. The solution was cooled to RT and partitioned between water and EtOAc. The aqueous layer was extracted with EtOAc (3×). The combined organic layers were washed with brine, dried over Na₂SO₄, filtered and concentrated. The crude oil was purified by flash chromatography (gradient 100:0 to 65:35 hexanes/EtOAc) to afford 2.2 g (45%) as a clear oil.

Step 8

To a solution of the carbamate from step 7 (2.1 g, 3.1 mmol) in EtOH (50 mL) was added 4 N HCl (20 mL, in dioxane). The solution was stirred at rt for 3 h. The solution was concentrated. The oil was redissolved in MeCN (10 mL). To this solution was added the pyrimidine acid 5 (705 mg, 4.6 mmol), EDCl (883 mg, 4.6 mmol), HOBt (621 mg, 4.6 mmol) and iPr₂NEt (5.4 mL, 31.0 mmol). The solution was stirred at room temperature, for 16 hours. The solution was concentrated, partitioned between EtOAc and NaHCO₃ (aq.). The aqueous layer was extracted with EtOAc (3×). The combined organic layers were washed with brine, dried over Na₂SO₄, filtered and concentrated. The crude oil was purified by flash chromatography (1:1 Acetone/hexanes) to afford 1.5 g of the amide.

Step 9

To a solution of the ethyl ester from step 8 (1.0 g, 1.7 mmol) in EtOH (30 mL) was added 2 M LiOH (1.7 mL, 3.4 mmol). The solution was stirred at room temperature for 6 hours. The solution was concentrated to afford the lithium salt of the carboxylate.

Step 10

To a solution of the carboxylate from Step 9 (95 mg, 0.16 mmol) in MeCN (1 mL) was added cyclobutylamine (0.041 mL, 0.48 mmol), EDCl (92 mg, 0.48 mmol), HOBt (66 mg, 0.48 mmol) and iPr₂NEt (0.084 mL, 0.48 mmol). The solution was stirred at room temperature for 16 hours. The solution was concentrated, partitioned between EtOAc and 1 M NaOH (aq.). The aqueous layer was extracted with EtOAc (3×). The combined organic layers were washed with brine, dried over Na₂SO₄, filtered and concentrated. The crude product was purified by prep TLC (2:1 acetone/hexanes) to afford 18 mg (18%) as a clear oil. The HCl salt of this product was formed by the addition of 4N HCl (dioxane) followed by evaporation. HRMS calc for $C_{37}H_{49}N_6O_3(MH^+)$: 625.3866; found: 625.3827.

EXAMPLE 4

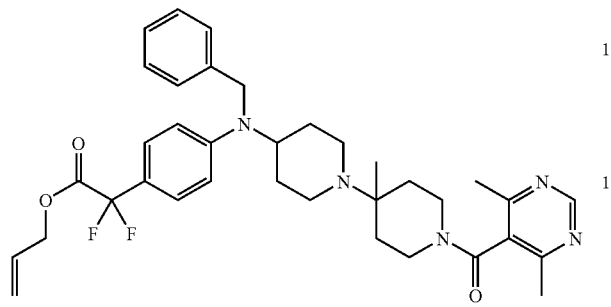

Step 1

To a solution of 4-aminophenylacetic acid (10 g, 66.2 mmol) in allyl alcohol (50 mL) was added $H_2SO_4$ (4.1 mL, 79.3 mmol). The solution was heated to reflux for 3 days. The solution was then concentrated and partitioned between $NaHCO_3$ aq. and $CH_2Cl_2$. The aqueous layer was extracted with $CH_2Cl_2$ (3×). The combined organic layers were dried over $Na_2SO_4$, filtered and concentrated.

Step 2

The aniline from step 1 (5.1 g, 26.7 mmol) was treated with ketone 3 (7.9 g, 26.7 mmol), acetic acid (3.1 mL, 53.4 mmol) and sodium triacetoxyborohydride (17 g, 80.1 mmol) according to the conditions described in step 3 of example 1. The product (4.3 g, 34%) after purification by flash chromatography (gradient 2:1 to 1:0 EtOAc/hexanes) was obtained as a light yellow oil.

Step 3

The aniline from step 2 (4.3 g, 9.1 mmol) in DMF (30 mL) was treated with benzyl bromide (3.27 mL 27.4 mmol), potassium iodide (604 mg, 3.64 mmol), and $Cs_2CO_3$ (8.9 g, 27.4 mmol) under the conditions described in step 4 of example 1. The product (4.6 g) (90%) after purification by flash chromatography (1:1 EtOAc/hexanes) was obtained as a yellow oil.

Step 4

To the allyl ester from step 3 (1.16 g, 2.1 mmol) in anhydrous THF (50 mL) at −78° C. was slowly added a solution of potassium bis(trimethylsilyl) amide (1 M in hexanes, 6.2 mmol). The solution was stirred at −78° C. for 5 min. A solution of N-fluorobenzenesulfonamide (1.95 g, 6.2 mmol) in THF (10 mL) was added to the solution of the enolate and the resultant solution was stirred at −78° C. for 20 min. Water was poured into the cold reaction mixture. After the mixture warmed to room temperature the aqueous layer was extracted with EtOAc (3×). The combined organic layers were washed with brine, dried over $Na_2SO_4$, filtered and concentrated. The crude product was purified by flash chromatography (gradient 100:0 to 65:35 hexanes/EtOAc) to afford 660 mg (53%) as an orange oil.

Step 5

The t-butyl carbamate from step 4 (685 mg, 1.12 mmol) in $CH_2Cl_2$ (6 mL) was treated with TFA (3 mL) under the conditions of step 5 of example 1. After the workup the crude free amine was taken up in MeCN (3 mL) was treated with the pyrimidine 5 (136 mg, 1.54 mmol), EDCl (296 mg, 1.54 mmol), HOBt (208 mg, 1.54 mmol) and iPrNEt (0.532 mL, 3.0 mmol) under the conditions described in step 6 of example 1. The amide product (190 mg, 27%) after purification by flash chromatography (gradient 1:9 to 2:3 acetone/hexanes) as a clear oil. The HCl salt of this product was formed by the addition of 4N HCl (dioxane) followed by evaporation. HRMS calc for $C_{36}H_{44}F_2N_5O_3(MH^+)$: 632.3412; found: 632.3442.

EXAMPLE 5

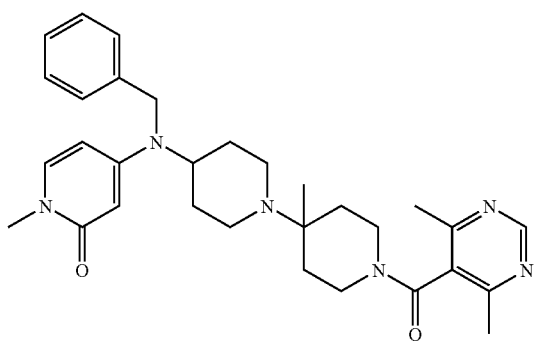

Step 1

To a solution of 4-chloro-2-hydroxypyridine (500 mg, 3.86 mmol) in benzene (8 mL) was added $K_2CO_3$ (1.6 g, 11.6 mmol), iodomethane (2.3 mL, 11.6 mmol) and tetrabutylammonium iodide (144 mg, 0.39 mmol). The mixture was stirred at room temperature for 24 hours. Water was added and the mixture was extracted with EtOAc (3×). The combined organic layers were dried over $Na_2SO_4$, filtered, and concentrated. The crude product was purified by prep TLC (1:1 hexanes/acetone) to afford 449 mg of product (81%) as a crystalline solid.

Step 2

The ketone 3 (5.0 g, 16.9 mmol) in $CH_2Cl_2$ was treated with benzylamine (1.67 mL, 15.3 mmol), sodium triacetoxyborohydride (3.89 g, 18.4 mmol), and acetic acid (1.1 mL, 18.4 mmol) under the conditions described in step 3 of example 1. The product (5.79 g, 98%) was obtained after flash chromatography (20:1 $CH_2Cl_2$/7N $NH_3$ in MeOH).

Step 3

To the amine from step 2 (270 mg, 0.70 mmol) in toluene (3 mL) was added the chloride from step 1 (100 mg, 0.70 mmol), palladium(II)acetate (31 mg, 0.14 mmol), sodium t-butoxide (270 mg, 2.8 mmol), and tri-t-butyl phosphine (110 mg, 0.56 mmol). The mixture was heated to 110° C. for 19 h. The mixture was cooled to room temperature, diluted with EtOAc, and filtered through Celite. To the filtrate was added 1 M NaOH. The aqueous layer was extracted with EtOAc (2×). The combined organic layers were washed with brine, dried over $Na_2SO_4$, filtered and concentrated. The crude product was purified by prep TLC (1:1 hexanes/acetone) to afford the product (58 mg, 17%) as an orange oil.

Step 4

The t-butyl carbamate from step 3 (58 mg, 0.12 mmol) in MeOH (1 mL) was treated with 4 N HCl (0.3 mL, in dioxane) under the conditions of step 8 example 3. The crude HCl salt was treated with the pyrimidine acid 5 (55 mg, 0.36 mmol), EDCl (46 mg, 0.24 mmol), HOBt (32 mg, 0.24 mmol) and iPr$_2$NEt (0.84 mL, 0.48 mmol) under the conditions in step 8 example 3. The crude product was purified by prep TLC (95:5 EtOAc/triethylamine) to afford 46 mg (66%) as an oil. The HCl salt of this product was formed by the addition of 4N HCl (dioxane) followed by evaporation. HRMS calc for C$_{31}$H$_{41}$N$_6$O$_2$(MH$^+$): 529.3291; found: 529.3269.

EXAMPLE 6

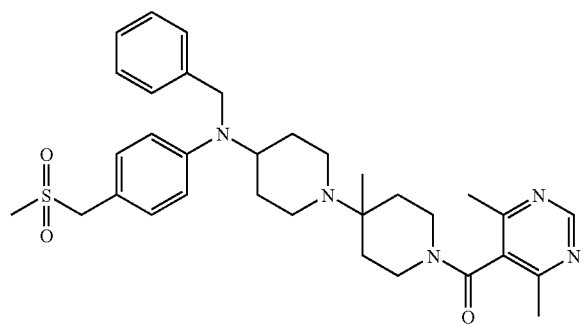

Step 1

A solution of 4-aminobenzyl alcohol (1.23 g, 10 mmol) in DMF (10 mL) was treated with t-butyldimethylsilyl chloride (1.5 g, 10 mmol) and imidazole (820 mg, 12 mmol) as described in step 4 example 3. The crude product (1.98 g) was used without further purification.

Step 2

The aniline from step 1 (1.98 g, 8.35 mmol) in CH$_2$Cl$_2$ (30 mL) was treated with ketone 3 (2.47 g, 8.35 mmol), sodium triacetoxyborohydride (3.52 g, 16.7 mmol), and acetic acid (1.0 mL, 16.7 mmol) under the conditions described in step 3 of example 1. The product (1.7 g, 39%) was obtained after purification by flash chromatography (7:3 hexanes/acetone).

Step 3

The aniline from step 2 (1.7 g, 3.29 mmol) in DMF (15 mL) was treated with benzyl bromide (0.59 mL, 4.93 mmol), Cs$_2$CO$_3$ (2.14 g, 6.58 mmol) and potassium iodide (10 mg) under the conditions described in step 4 of example 1. The product (1.84 g, 92%) was obtained after purification by flash chromatography (7:3 hexanes/acetone).

Step 4

The t-butyl carbamate from step 3 (500 mg, 0.82 mmol) in 2:5 CH$_2$Cl$_2$/MeOH (7 mL) was treated with added 4 N HCl (6 mL, in dioxane) under the conditions of step 8 example 3. The free amine in CH$_2$Cl$_2$ (3 mL) was treated with pyrimidine 5 (105 mg), HOBt (123 mg), EDCl (175 mg), and iPr$_2$NEt (147 mg) under the conditions described in step 6 example 1. The product was obtained after purification by prep TLC.

Step 5

The benzyl alcohol from step 4 (50 mg, 0.09 mmol) in dioxane (3 mL) was treated with water (5 drops), 4 N HCl (aq.) (0.1 mL), and methanesulfinic acid sodium salt (51 mg, 0.43 mmol). The solution was stirred at 55° C. for 4 hours. The mixture was treated with NaHCO$_3$(aq.) and extracted with EtOAc. The organic layer was dried over Na$_2$SO$_4$, filtered and concentrated. The crude product was purified by prep TLC (9:1 CH$_2$Cl$_2$/MeOH) to afford the product (30 mg, 57%). The HCl salt of this product was formed by the addition of 4N HCl (dioxane) followed by evaporation. HRMS calc for C$_{33}$H$_{44}$N$_5$O$_3$S (MH$^+$): 590.3165; found: 590.3187.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. An example of this includes, but is not limited to, water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compound of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of the invention may also be administered orally, intravenously, intranasally or subcutaneously.

Preferably the compound is administered orally.

Preferably, the pharmaceutical preparation is in a unit dosage form. In such form, the preparation is subdivided into suitably sized unit doses containing a therapeutically effective amount of the compound having formula I.

The quantity of active compound in a unit dose of preparation may be varied or adjusted from about 10 mg to about 500 mg, preferably from about 25 mg to about 300 mg, more preferably from about 50 mg to about 250 mg, and most preferably from about 55 mg to about 200 mg, according to the particular application.

The actual dosage of the inventive compound employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 100 mg/day to about 300 mg/day, preferably 150 mg/day to 250 mg/day, more preferably about 200 mg/day, in two to four divided doses.

The doses and dosage regimens of the NRTIs, NNRTIs, PIs and other agents used in combination with the compounds of this invention will be determined by the attending clinician in view of the approved doses and dosage regimens in the package inserts or as set forth in the protocols, taking into consideration the age, sex and condition of the patient and the severity of the condition treated.

In a preferred embodiment, the compound of the present invention can be used to treat Human Immunodeficiency Virus by administering to a patient in need of such treatment a therapeutically effective amount of one or more compounds having formula I, preferably in combination with one or more pharmaceutically acceptable carriers. One or more, preferably one to four, antiviral agents useful in anti-HIV-1 therapy can be used in combination with the compound of the present invention. The antiviral agent or agents can be combined with one or more compounds of the present invention in a single dosage form. The one or more compounds of the present invention and the antiviral agent or agents may be administered in any order such as, for example, sequentially, concurrently, simultaneously and the like. The amounts of the various actives in such combination therapy may be different amounts (dosage amounts) or same amounts (dosage amounts). The various actives could also be present in fixed amounts in the same dosage form, e.g., 10 mg of a compound of claim 1 and 10 mg of an anti-viral agent present in a single tablet. An illustrative such "single tablet" would be, for example, the anti-cholesterol medication VYTORIN® (available from Merck Schering-Plough Pharmaceuticals, Kenilworth, N.J.).

The antiviral agents contemplated for use in combination with the compound of the present invention comprise nucleoside and nucleotide reverse transcriptase inhibitors, non-nucleoside reverse transcriptase inhibitors, protease inhibitors and other antiviral drugs listed below not falling within these classifications. Specific examples of antiviral agents include, but are not limited to, zidovudine, lamivudine, zalcitabine, didanosine, stavudine, abacavir, adefovir dipivoxil, lobucavir, BCH-10652, emitricitabine, beta-L-FD4, DAPD, lodenosine, nevirapine, delaviridine, efavirenz, PNU-142721, AG-1549, MKC-442, (+)-calanolide A and B, saquinavir, indinavir, ritonavir, nelfinavir, lasinavir, DMP-450, BMS-2322623, ABT-378, amprenavir, hydroxyurea, ribavirin, IL-2, IL-12, pentafuside, Yissum No. 11607 and AG-1549. In particular, the combinations known as HAART are contemplated for use in combination with the compound of this invention.

For combination treatment with more than one active agent, where the active agents are in separate dosage formulations, the active agents may be administered separately or in conjunction. In addition, the administration of one element may be prior to, concurrent to, or subsequent to the administration of the other agent.

Another aspect of the invention provides a method of treating solid organ transplant rejection, graft v. host disease, arthritis, rheumatoid arthritis, inflammatory bowel disease, atopic dermatitis, psoriasis, asthma, allergies or multiple sclerosis comprising administering to a patient in need of such treatment a therapeutically effective amount of one or more compounds of formula I, preferably in combination with one or more pharmaceutically acceptable carriers. In another embodiment, the method for treating solid organ transplant rejection, graft v. host disease, rheumatoid arthritis, inflammatory bowel disease or multiple sclerosis further comprises administering one or more other agents useful in the treatment of said diseases in combination with one or more compounds of formula I.

Agents known in the treatment of rheumatoid arthritis, transplant and graft v. host disease, inflammatory bowel disease and multiple sclerosis which can be administered in combination with the compound of the present invention are as follows:

solid organ transplant rejection and graft v. host disease: immune suppressants such as cyclosporine and Interleukin-10 (IL-10), tacrolimus, antilymphocyte globulin, OKT-3 antibody, and steroids;

inflammatory bowel disease: IL-10 (see U.S. Pat. No. 5,368,854), steroids and azulfidine;

rheumatoid arthritis: methotrexate, azathioprine, cyclophosphamide, steroids and mycophenolate mofetil;

multiple sclerosis: interferon-beta, interferon-alpha, and steroids.

Another aspect of the invention relates to a kit comprising in separate containers in a single package pharmaceutical composition for use in combination to treat Human Immunodeficiency Virus. In one container, a pharmaceutical composition comprises one or more compounds of formula I in one or more pharmaceutically acceptable carriers, and in separate containers, one or more pharmaceutical compositions comprising an effective amount of one or more antiviral agents or other agents useful in the treatment of Human Immunodeficiency Virus in one or more pharmaceutically acceptable carriers.

The goal of the HIV-1 therapy of the present invention is to reduce the HIV-1-RNA viral load below the detectable limit. The "detectable limit of HIV-1-RNA" in the context of the present invention means that there are fewer than about 200 to fewer than about 50 copies of HIV-1-RNA per ml of plasma of the patient as measured by quantitative, multi-cycle reverse transcriptase PCR methodology. HIV-1-RNA is preferably measured in the present invention by the methodology of Amplicor-1 Monitor 1.5 (available from Roche Diagnostics) or of Nuclisens HIV-1 QT-1.

Assays useful for determining the CCR5 antagonistic activity as well as the HIV replication inhibitory activity are described in detail in patent application, Serial No. IN01481K. The following assays were used to determine the CCR5 antagonistic activity and the HIV replication inhibitory activity of the compounds of the invention.

Chemotaxis Assay: The chemotaxis assay is a functional assay which characterizes the agonist vs. antagonist properties of the test compounds. The assay measures the ability of a non-adherent murine cell line expressing human CCR5 (BaF-550) to migrate across a membrane in response to either test compounds or natural ligands (i.e., RANTES, MIP-1β). Cells migrate across the permeable membrane towards compounds with agonist activity. Compounds that are antagonists not only fail to induce chemotaxis, but are also capable of inhibiting cell migration in response to known CCR5 ligands. The activity of the inventive compounds was also measured by the Chemitaxis assay.

Chemotaxis Assay procedure: Ba/F3-hCCR5 clone 550 (a.k.a. B550) cells were cultured in RPMI-1640 supplemented with 10% fetal bovine serum (FBS), 1×Pen-Strep, 1×Glutamax, 1×HEPES, 1×2-mercaptoethanol, and mIL-3 at 1 µg/L. All tissue culture reagents were obtained from Invitrogen (Carlsbad, Calif.), unless otherwise specified. FBS was obtained from Gemini Bio-Products, Woodland, Calif. Mouse IL-3 was obtained from R and D Systems, Minneapolis, Minn.

Human MIP-1β (hMIP-1β) was purchased from R and D Systems and was used at a final concentration of 1 nM in the assay. The compounds were reconstituted in DMSO and diluted in the chemotaxis assay medium, from 0.1 nM to 1000 nM (final concentrations).

For assay, the cells were washed twice in plain RPMI 1640 medium, and then resuspended at the appropriate concentration in the assay medium. The assay medium consisted 10% Ba/F3 media in RPMI 1640. The final density of cells for the assay was approximately cells at $2.5 \times 10^6$ per ml. Chemotaxis was performed using the 96-well ChemoTx system® with 5 micron filter pore size (NeuroProbe, Inc., Gaithersburg, Md., Cat. #:101-5).

The compounds were used in an antagonist chemotaxis setup according to the manufacturer's instructions. Briefly, each compound was mixed with hMIP-1β and approximately 29 μl of the mixture was placed in the bottom well of the 96-well ChemoTx system. The filter screen was placed on top and 25 μl of cells mixed with the appropriate concentration of compound was placed on the filter. The assembled plates were incubated for 2 hours at 37° C. in a humidified chamber. After incubation the cells were scraped off and the plate system is centrifuged for 5 minutes at 1000 rpm in an IEC Centra-8R centrifuge. The filter screen was removed and the ChemoTx plate was inverted onto a 96 well plated with a funnel plate. The plate system was centrifuged for 5 minutes at 1000 pm. The volume in the wells was brought to 100 μl with medium and the plates were rested for approximately 20 minutes. The number of migrating cells was measured using the Cell Titer Glo Luminescent Assay from Promega (Madison, Wis.), and the TROPIX TR717 Microplate Luminometer (PE Applied Biosystems, Boston, Mass.)) by following the manufacturer's instructions.

Luciferase Replication Assay:

Plasmids encoding the full length genome of HIV-1 pNL-4-Luc with the gp 120 V-3 loop replaced by the Bgl II fragment of HIV-1 ADA, YU-2 or HxB (ADA-Luc-FL, YU-2-Luc-FL and HxB-Luc-FL) were obtained from Dr. Susan Pontow (Washington University, St. Louis Mo.). Replication-competent luciferase reporter virus stocks were generated by transfection of plasmids into 293T cells using Superfect (Qiagen) or Mirus transfection reagents. Viral stocks were collected 48 hours following transfection and titered for luciferase production on U-87-CCR5 or CXCR4 cells. U87-CD4-CCR5 cells (104/well) were plated in 96-well cell culture plates and incubated overnight. Media was removed and replaced with 50 μl of fresh culture media (DMEM, 10% FCS) and 50 μl of compound diluted in culture medium. Cells were incubated with compound at 37° C. for 1 hour. The resultant supernatant was removed and replaced with 20 μl of media containing compound and infected with an equal volume of diluted or undiluted virus stock at 37° C. for 3-4 hours. The cells were washed once with DMEM, and 200 μl of media containing compound was added. The cultures were incubated for 3 days, the cells lysed in luciferase lysis buffer (Promega, Madison, Wis.) and transferred to Immulon plates (Dynex Technologies, Chantilly Va.). An equal volume of luciferase substrate (Promega, Madison Wis.) was added to lysates and the plates read immediately in a Wallac Luminometer. Fifty and ninety percent inhibitory concentrations were determined using GraphPad PRISM software.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by the structural formula:

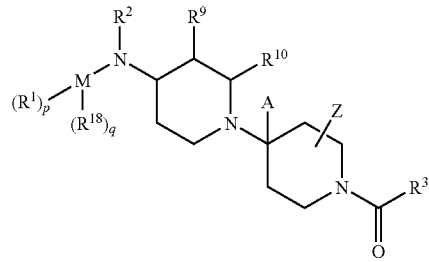

or a pharmaceutically acceptable salt thereof; wherein:
p is 1;
M is phenyl;
$R^1$ is selected from the group consisting of:
  -alkyl-C(O)-heterocyclyl,
  -haloalkyl-C(O)$OR^5$,
  —S(O$_2$)(hydroxyalkyl),
  -alkyl-C($R^5$)(=N—O$R^6$), and
  —S(O$_2$)(heterocyclyl);
$R^2$ is selected from the group consisting of aryl, and arylalkyl wherein said aryl is phenyl, and said arylalkyl is benzyl or phenethyl;
$R^3$ selected from the group consisting of aryl, 6-membered heteroaryl, and 6-membered heteroaryl-N-oxide, wherein each of said aryl, heteroaryl, and heteroaryl-N-oxide is unsubstituted or independently substituted with 1-4 substituents which can be the same or different each substituent being independently selected from the group consisting of $R^{11}$, $R^{12}$, $R^{13}$ and $R^{14}$, wherein said aryl is phenyl, said 6-membered heteroaryl is pyrimidinyl, and said heteroaryl-N-oxide is pyrimidinyl-N-oxide;
$R^5$ and $R^6$ can be the same or different, each being independently selected from the following group consisting of H, alkyl, cycloalkyl, heterocyclyl, aryl, arylalkyl and heteroaryl;
$R^9$, $R^{10}$ and Z can be the same or different each being independently selected from the group consisting of hydrogen and alkyl;
$R^{11}$ and $R^{12}$ can be the same or different each being independently selected from the group consisting of alkyl, —NR$^{19}$R$^{20}$, and —OH;
$R^{13}$ is selected from the group consisting of H, —N(R$^{20}$)C(O)N(R$^{20}$R$^{21}$), —N(H)S(O$_2$)alkyl, and —N(H)S(O$_2$)cycloalkyl;
$R^{14}$ is alkyl;
$R^{19}$, $R^{20}$ and $R^{21}$ can each be the same or different and are each independently selected from the group consisting of H, alkyl, aryl, arylalkyl, and cycloalkyl; and
A is selected from the group consisting of H, alkyl, and alkenyl.

2. The compound of claim 1, wherein $R^1$ is selected from the group consisting of:
  —(C1-C6)alkyl-C(O)-heterocyclyl,
  -halo(C1-C6)alkyl-C(O)OR$^5$,
  —S(O$_2$)(hydroxy(C1-C6)alkyl),
  —(C1-C6)alkyl-C(R$^5$)(=N—OR$^6$), and
  —S(O$_2$)(heterocyclyl).

3. The compound of claim 1, wherein A is methyl.
4. The compound of claim 1, wherein Z is H.
5. The compound of claim 1, wherein $R^1$ is —(CH$_2$)—C(O)-heterocyclyl, or —(CH$_2$)—C($R^5$)(=N—O$R^6$); and A is methyl.
6. The compound of claim 1, wherein $R^1$ is selected from the group consisting of:

—CH$_2$(C=O)-morpholine,
—CH(CH$_3$)(C=O)-morpholine,
—C(CH$_3$)$_2$—C(=O)-morpholine,
—C(CH$_3$)$_2$—C(=O)-pyrrolidine, and
—C(CH$_3$)$_2$—C(=O)-piperidine.

7. A compound selected from the group consisting of:

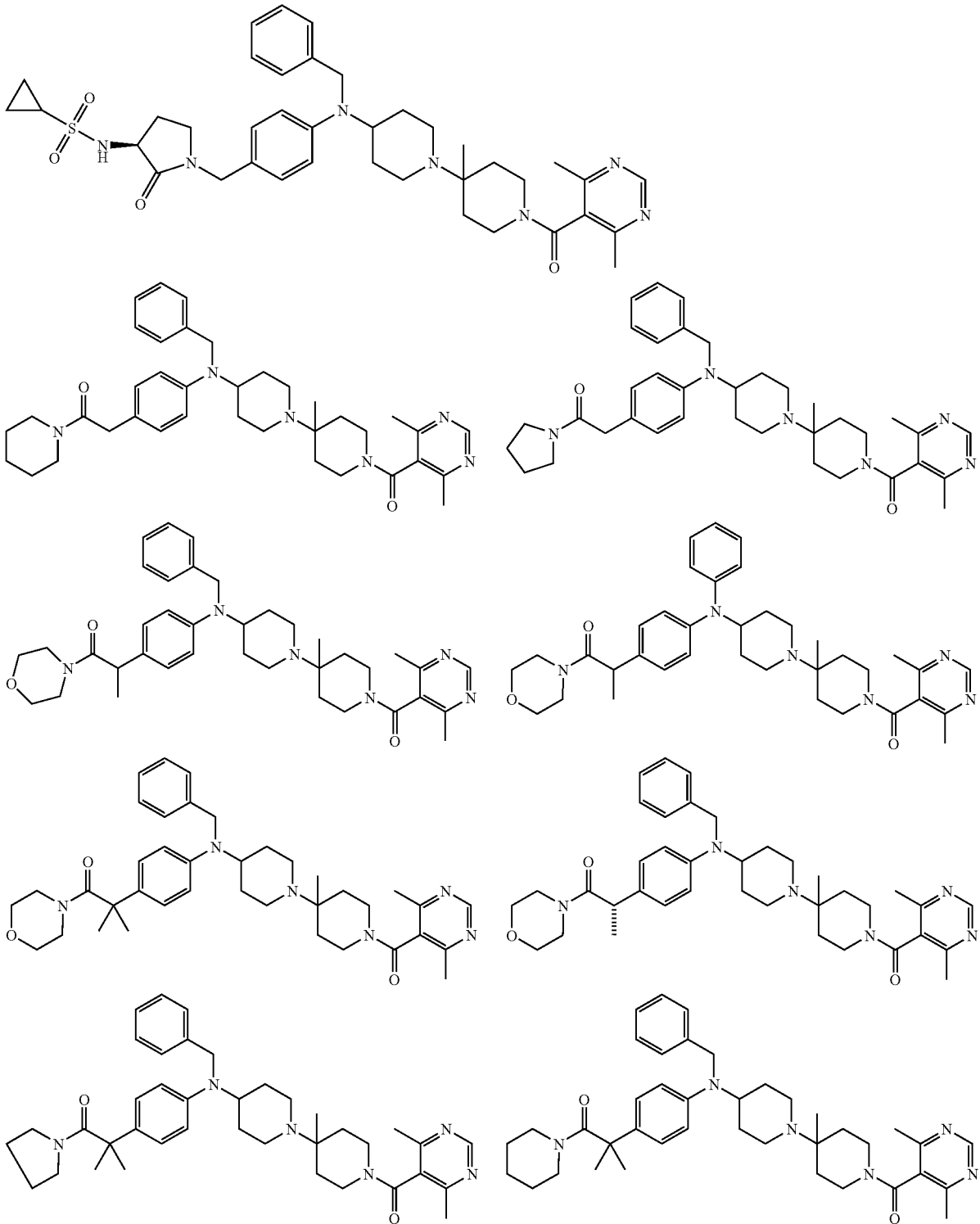

-continued
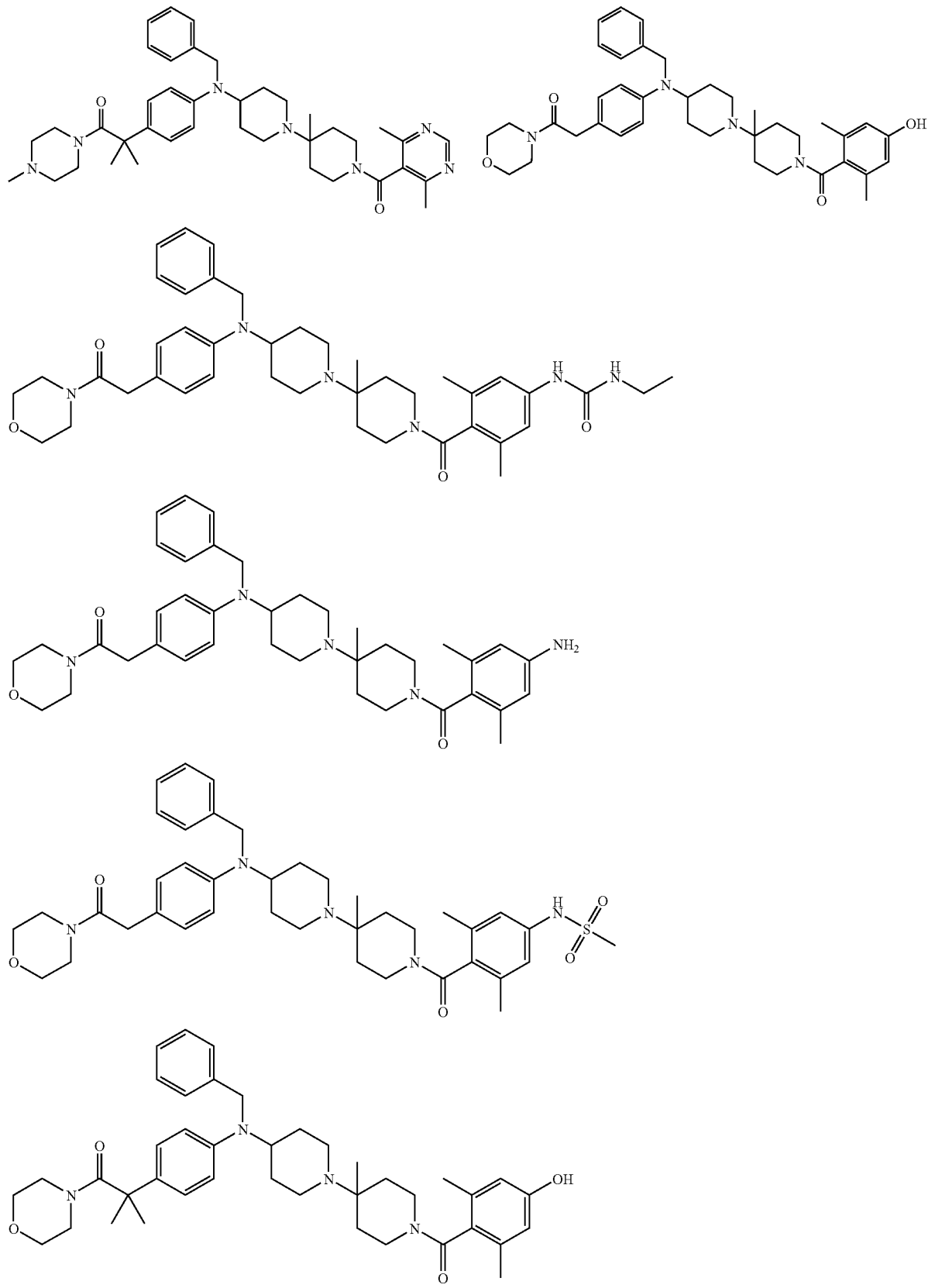

-continued
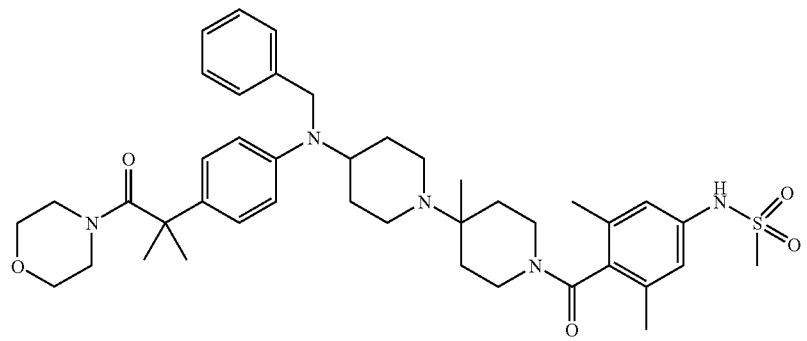
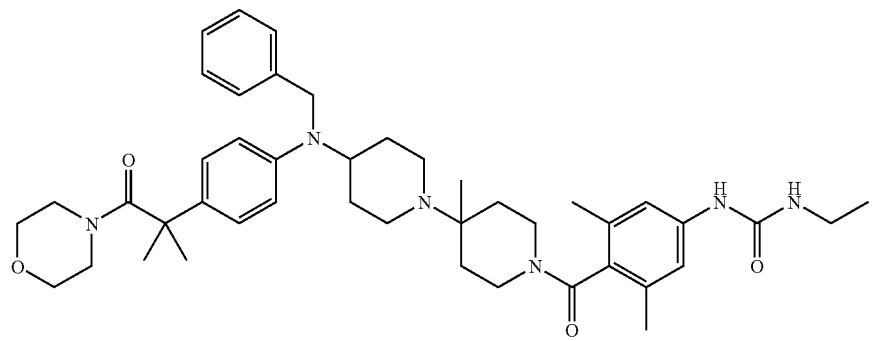
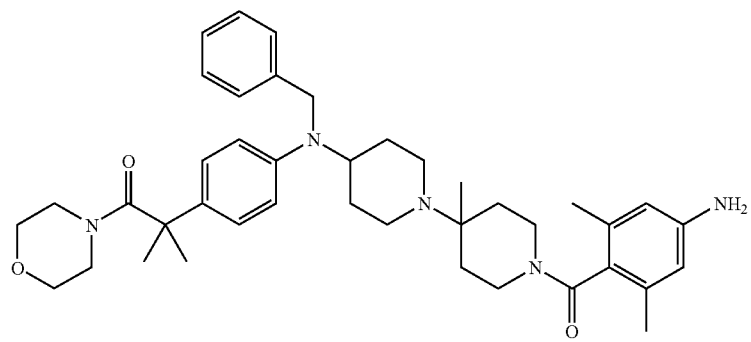
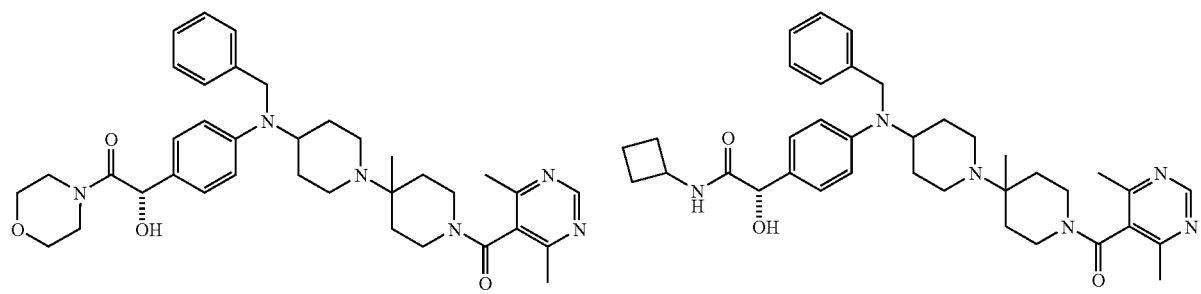
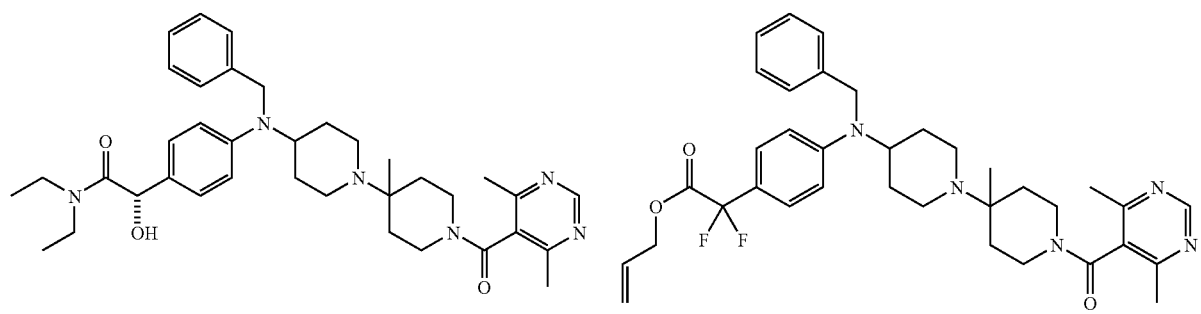

-continued
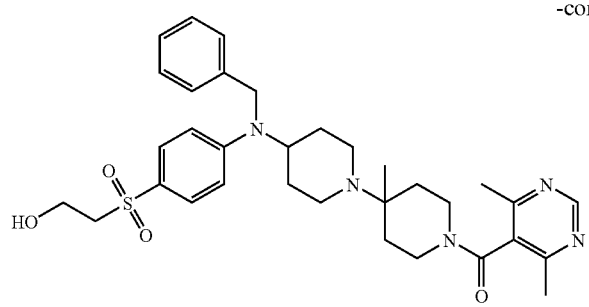
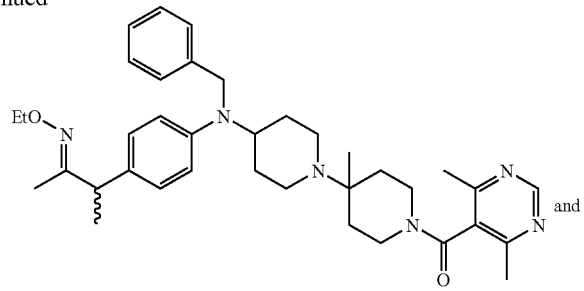 and
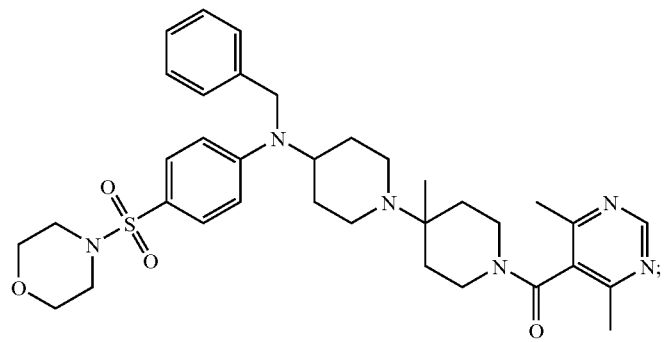
or a pharmaceutically acceptable salt thereof.
8. A compound selected from the group consisting of:
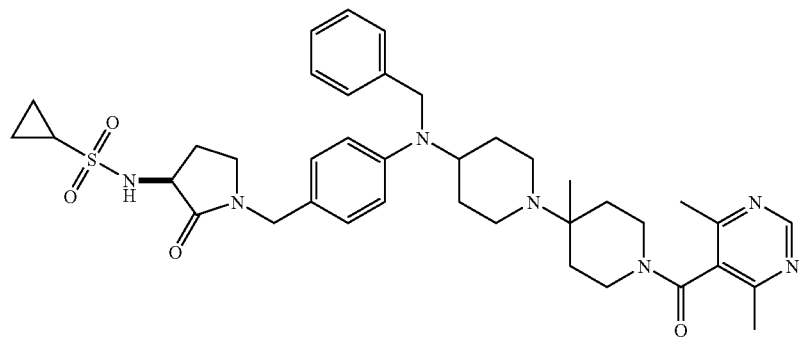
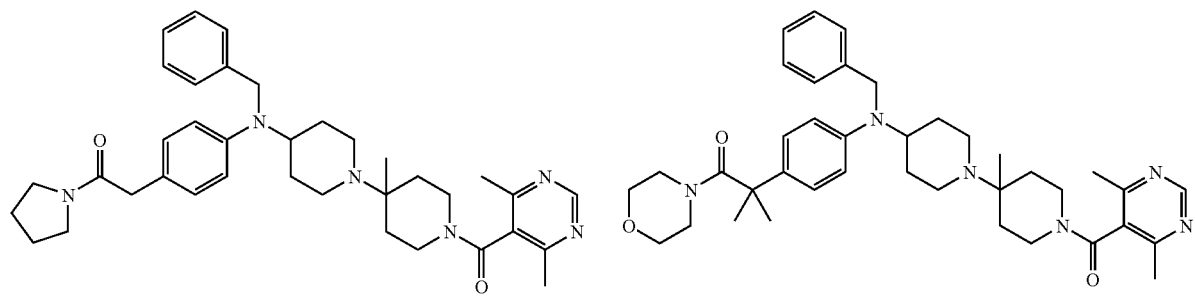

-continued
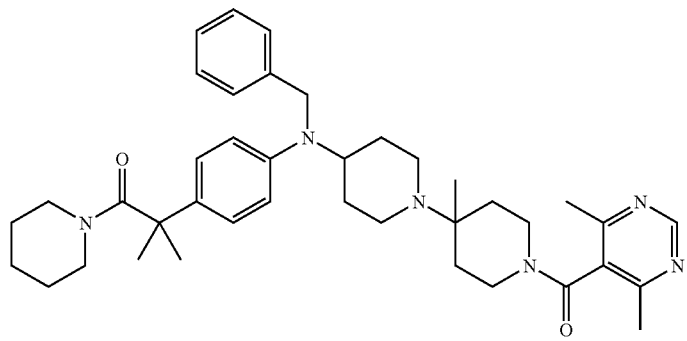
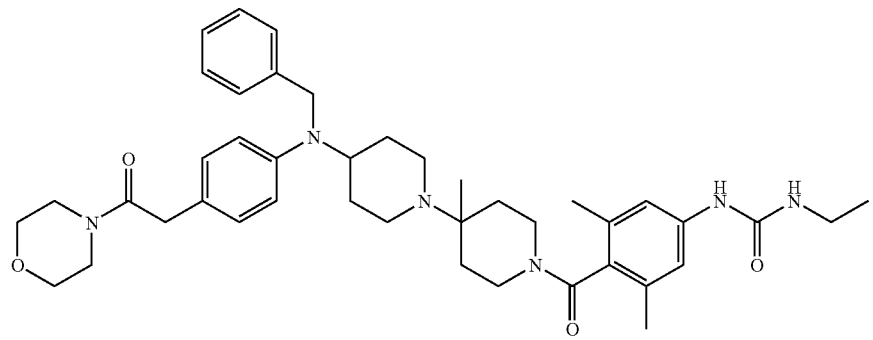
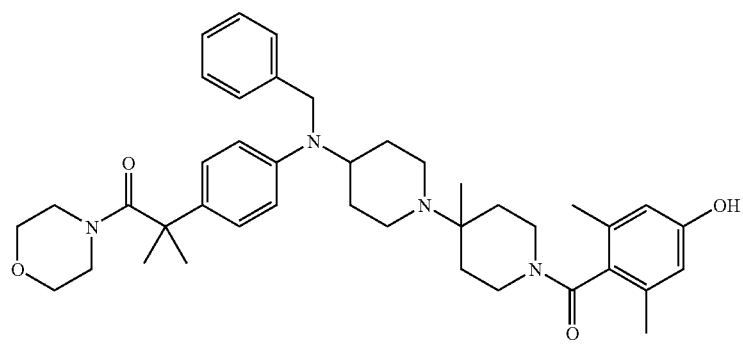
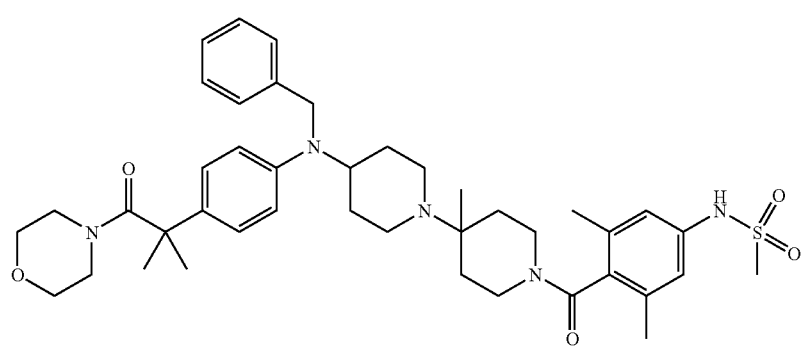
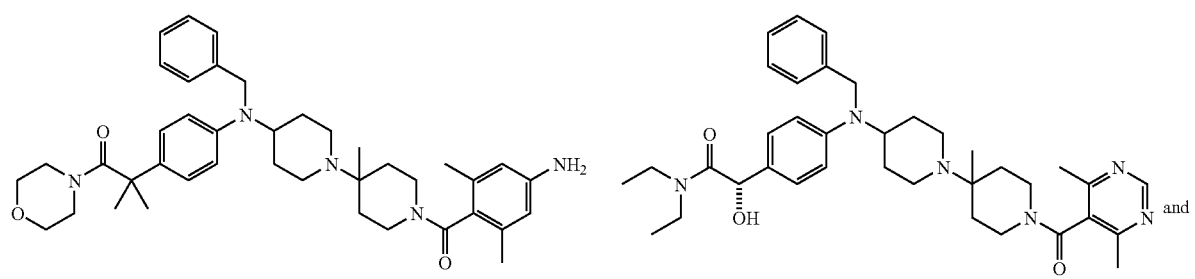
and

-continued
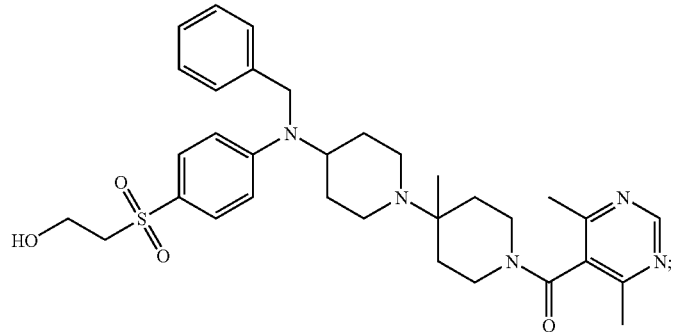
or a pharmaceutically acceptable salt thereof.
9. A compound selected from the group consisting of:
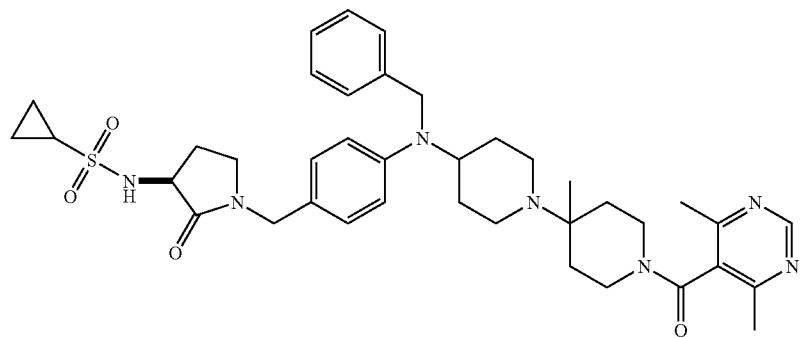
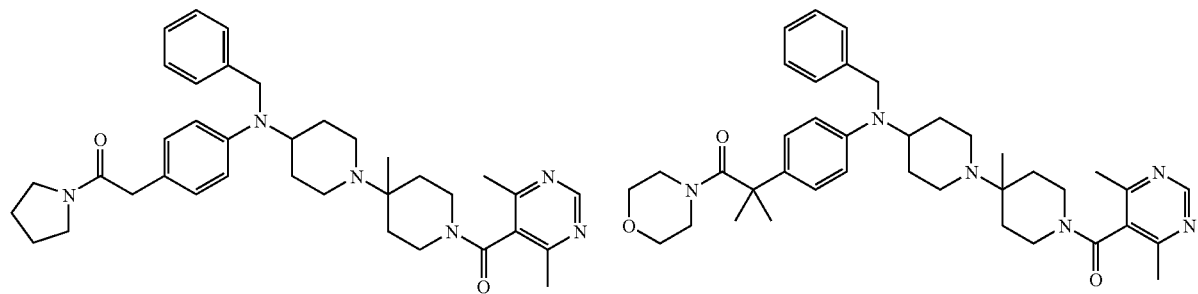
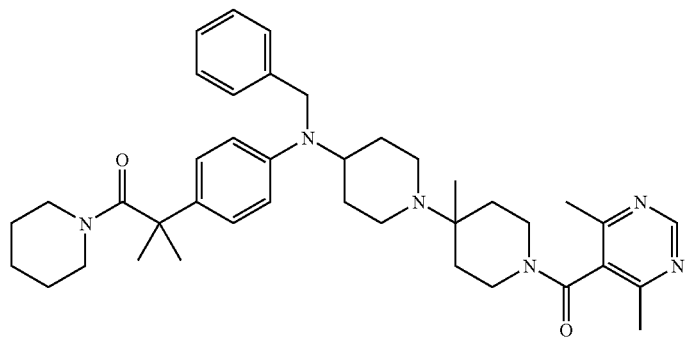

-continued
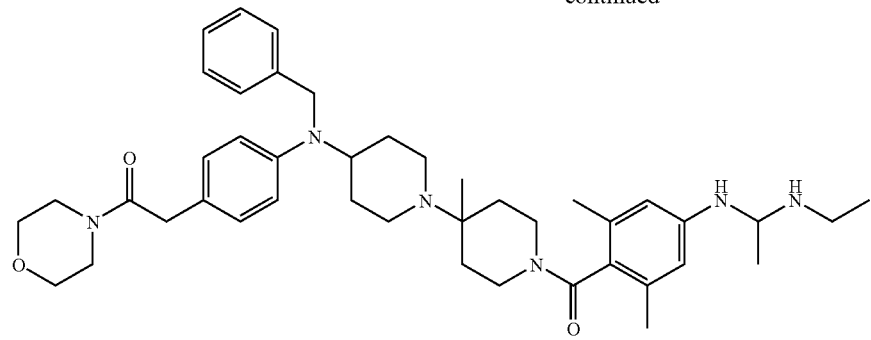
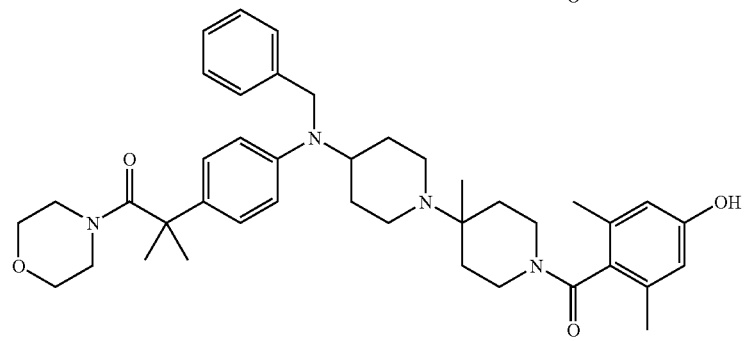
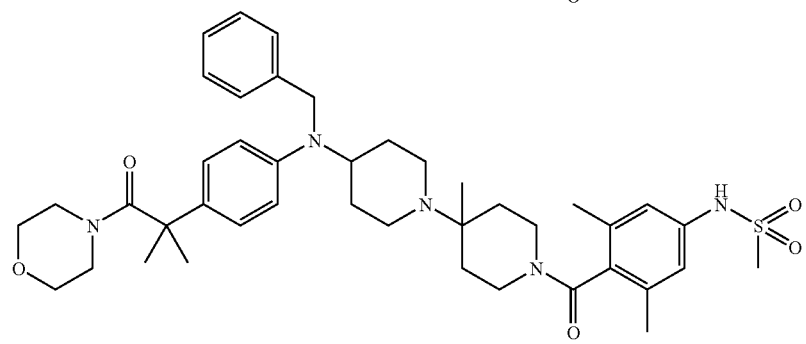
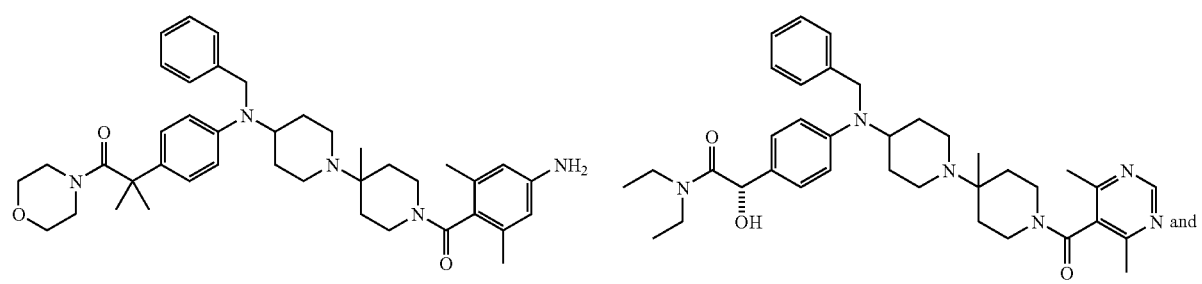
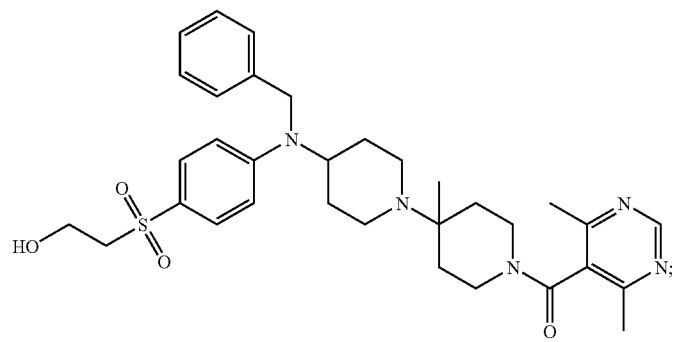
or a pharmaceutically acceptable salt thereof.

10. A pharmaceutical composition comprising a therapeutically effective amount of at least one compound of claim 1 or a pharmaceutically acceptable salt thereof in combination with at least one pharmaceutically acceptable carrier.

11. A pharmaceutical composition comprising a therapeutically effective amount of at least one compound of claim 8 or a pharmaceutically acceptable salt thereof in combination with at least one pharmaceutically acceptable carrier.

12. A pharmaceutical composition comprising a therapeutically effective amount of at least one compound of claim 9 or a pharmaceutically acceptable salt thereof in combination with at least one pharmaceutically acceptable carrier.

13. A compound of claim 1 or a pharmaceutically acceptable salt thereof in isolated and purified form.

14. A pharmaceutical composition comprising a therapeutically effective amount of at least one compound of claim 7 or a pharmaceutically acceptable salt thereof in combination with at least one pharmaceutically acceptable carrier.

* * * * *

UNITED STATES PATENT AND TRADEMARK OFFICE
CERTIFICATE OF CORRECTION

PATENT NO. : 7,652,142 B2
APPLICATION NO. : 10/979075
DATED : January 26, 2010
INVENTOR(S) : Miller et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 738 days.

Signed and Sealed this

Twenty-third Day of November, 2010

David J. Kappos
*Director of the United States Patent and Trademark Office*